(12) United States Patent
Orbay et al.

(10) Patent No.: US 11,432,859 B2
(45) Date of Patent: *Sep. 6, 2022

(54) HOOK PLATE AND HOOK PLATE SYSTEM

(71) Applicant: SKELETAL HOLDINGS, LLC, Miami, FL (US)

(72) Inventors: Jorge L. Orbay, Miami, FL (US); Thomas H. Norman, Miami, FL (US); Juan Salcedo, Miami, FL (US)

(73) Assignee: SKELETAL HOLDINGS, LLC, Miami, FL (US)

( * ) Notice: Subject to any disclaimer, the term of this patent is extended or adjusted under 35 U.S.C. 154(b) by 318 days.

This patent is subject to a terminal disclaimer.

(21) Appl. No.: 16/828,588

(22) Filed: Mar. 24, 2020

(65) Prior Publication Data

US 2020/0281632 A1    Sep. 10, 2020

Related U.S. Application Data

(63) Continuation of application No. 13/604,931, filed on Sep. 6, 2012, now Pat. No. 10,603,090, which is a (Continued)

(51) Int. Cl.
*A61B 17/80* (2006.01)
*A61B 17/86* (2006.01)
(Continued)

(52) U.S. Cl.
CPC ............ *A61B 17/808* (2013.01); *A61B 17/80* (2013.01); *A61B 17/8004* (2013.01);
(Continued)

(58) Field of Classification Search
CPC . A61B 17/80; A61B 17/8004; A61B 17/8009; A61B 17/8014; A61B 17/8023;
(Continued)

(56) References Cited

U.S. PATENT DOCUMENTS 3,824,995 A * 7/1974 Getscher ............. A61F 2/30739
606/281
5,810,822 A * 9/1998 Mortier ................ A61B 17/809
606/101

(Continued)

*Primary Examiner* — Amy R Sipp
(74) *Attorney, Agent, or Firm* — Lott & Fischer, PL

(57) ABSTRACT

A hook plate for use in conjunction with a fracture fixation plate, said fracture fixation plate including a bone contacting surface and an opposite surface, said hook plate comprising a substantially rigid plate having a first portion and a second portion; the first portion adapted for slidable engagement with, said opposite surface of said fracture fixation plate; the second portion configured to wrap around an edge of said fracture fixation plate to engage with a bone fragment and reduce a fracture; the first portion being substantially flat and defining a first portion plane; the second portion having at least two projections which curve downward to a position below the first portion plane and terminate in hook ends adapted to engage with said bone fragment; the first portion including a slot that transects said hook plate from a surface of said hook plate that faces the fracture fixation plate to an opposing surface of said hook plate for engagement with a fastener on said opposite surface of said fracture fixation plate; said slot being elongated; and the first portion including an elongate member extending distally away from the first portion and upward to a position above the first portion, said elongate member adapted to aid in the tensioning of the hook plate prior to tightening of the fastener.

8 Claims, 27 Drawing Sheets

Related U.S. Application Data continuation-in-part of application No. 13/366,886, filed on Feb. 6, 2012, now Pat. No. 8,814,918.

(60) Provisional application No. 61/595,986, filed on Feb. 7, 2012, provisional application No. 61/536,316, filed on Sep. 19, 2011, provisional application No. 61/531,485, filed on Sep. 6, 2011, provisional application No. 61/442,595, filed on Feb. 14, 2011.

(51) Int. Cl.
   *A61B 17/88* (2006.01)
   *A61B 17/17* (2006.01)
   *A61B 90/00* (2016.01)

(52) U.S. Cl.
   CPC ........ *A61B 17/809* (2013.01); *A61B 17/8061* (2013.01); *A61B 17/8085* (2013.01); *A61B 17/864* (2013.01); *A61B 17/8863* (2013.01); *A61B 17/1728* (2013.01); *A61B 17/8057* (2013.01); *A61B 17/863* (2013.01); *A61B 2090/037* (2016.02); *A61B 2090/3966* (2016.02)

(58) Field of Classification Search
   CPC .............. A61B 17/8061; A61B 17/808; A61B 17/8085; A61B 17/809; A61B 17/82; A61B 17/8866
   USPC ...................................... 606/70, 71, 280–299
   See application file for complete search history.

(56) References Cited

U.S. PATENT DOCUMENTS

| | | | | |
|---|---|---|---|---|
| 2002/0143336 | A1* | 10/2002 | Hearn | A61B 17/8009 606/213 |
| 2002/0177850 | A1* | 11/2002 | Bremer | A61B 17/688 606/70 |
| 2005/0234458 | A1* | 10/2005 | Huebner | A61B 17/8061 606/71 |

* cited by examiner

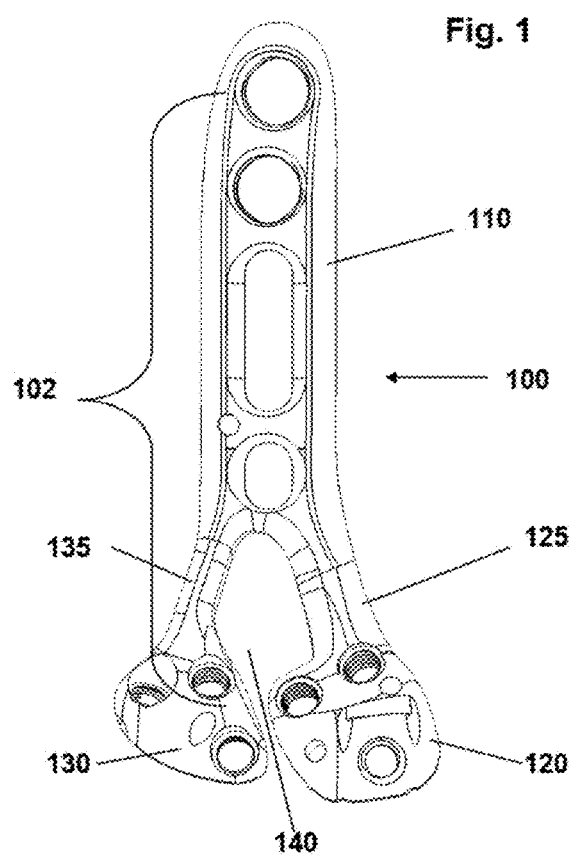
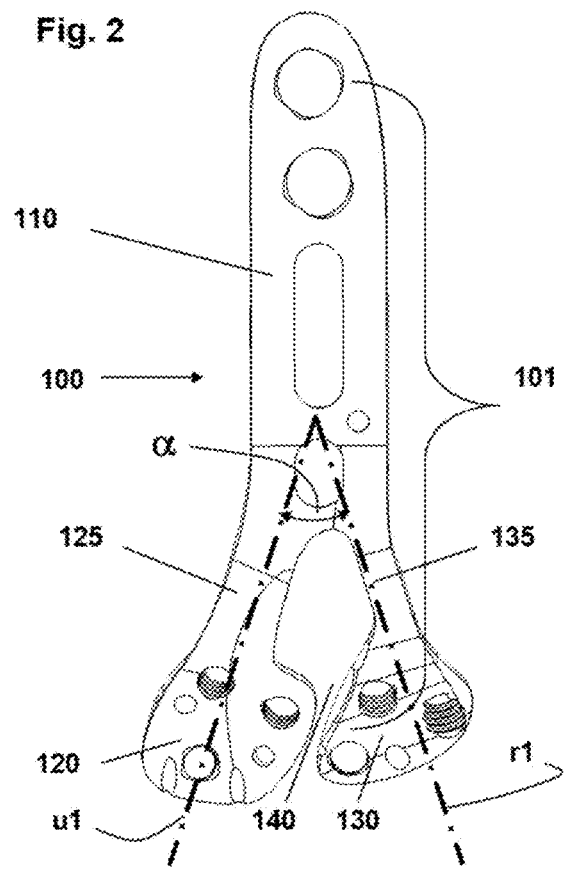

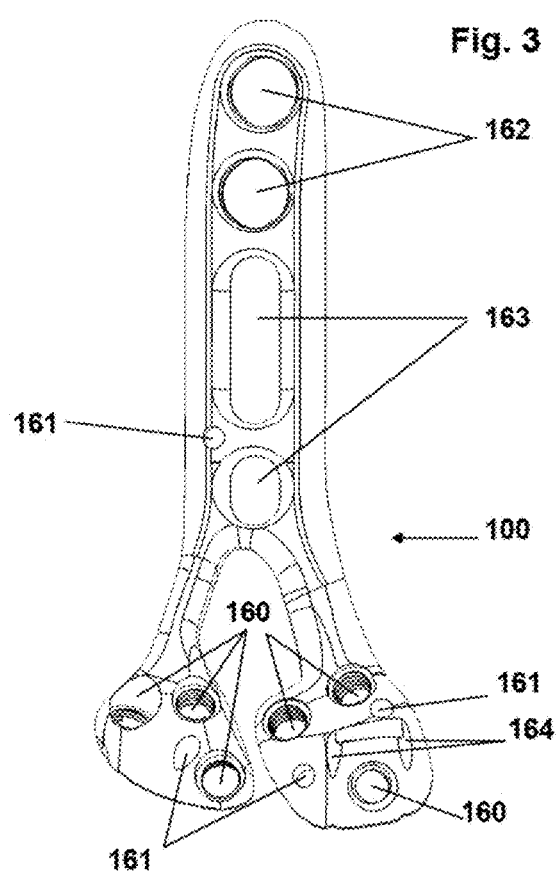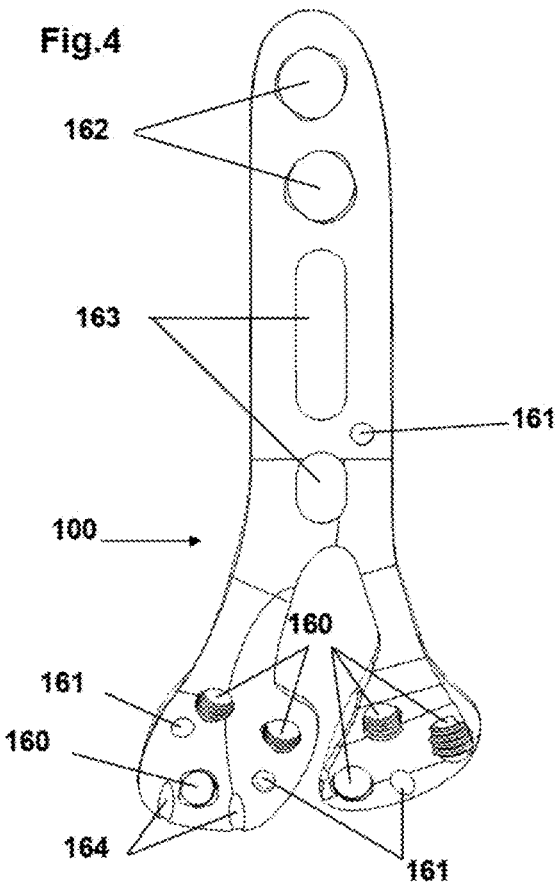

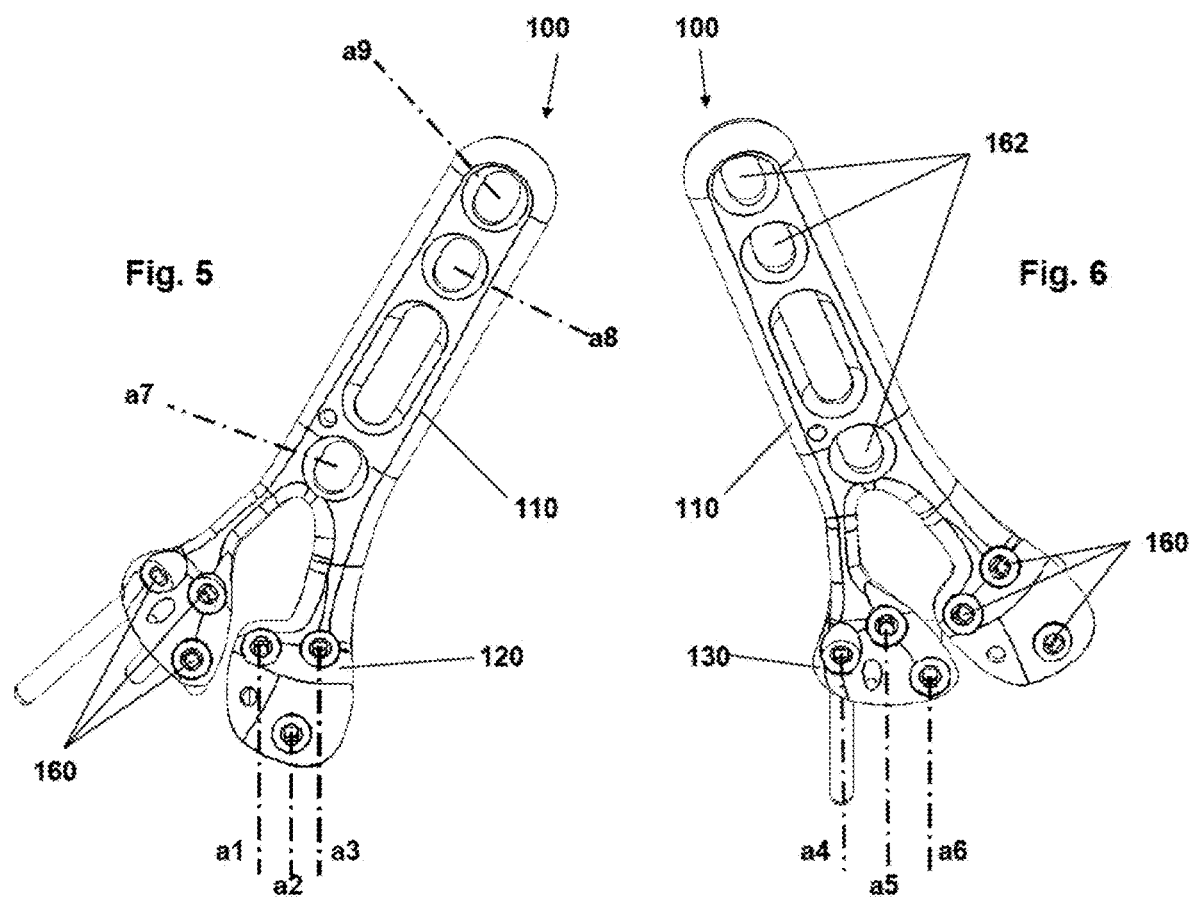

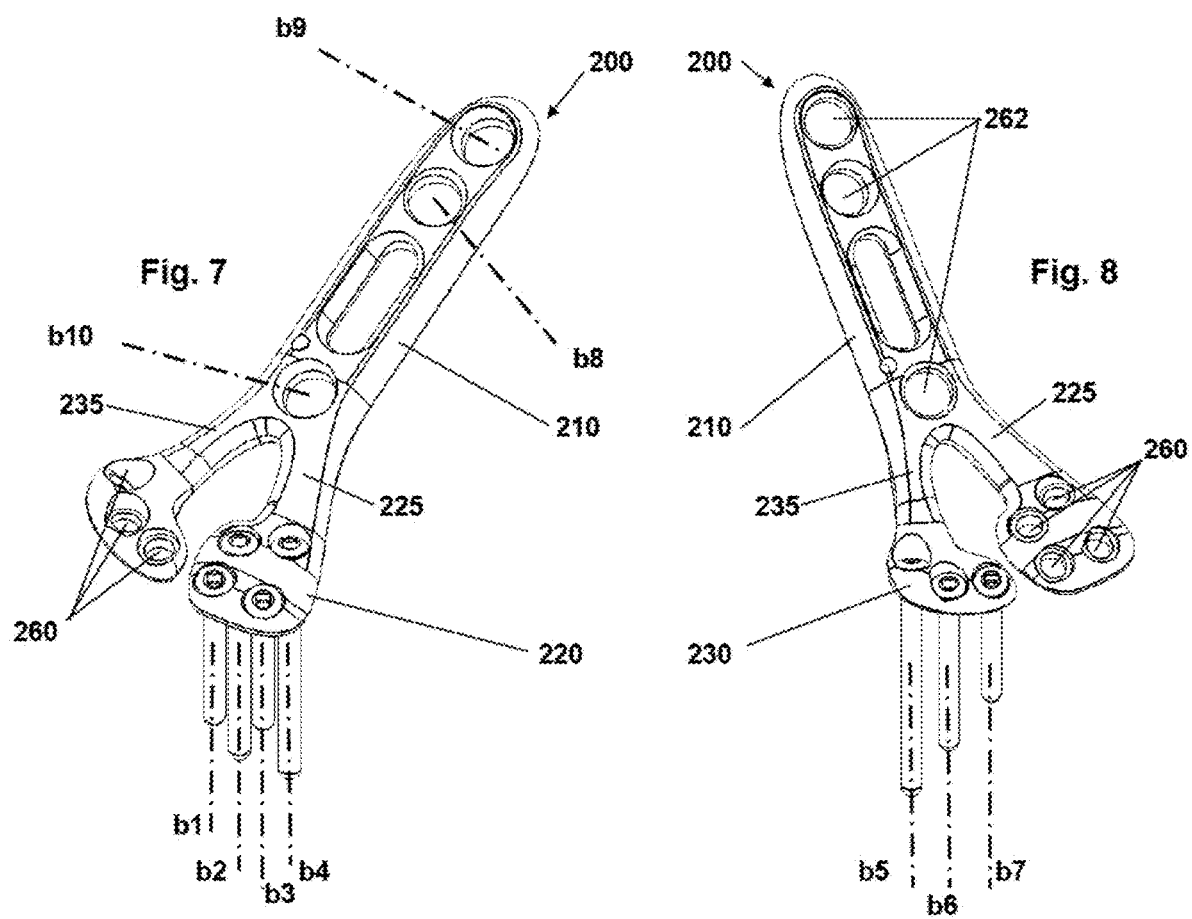

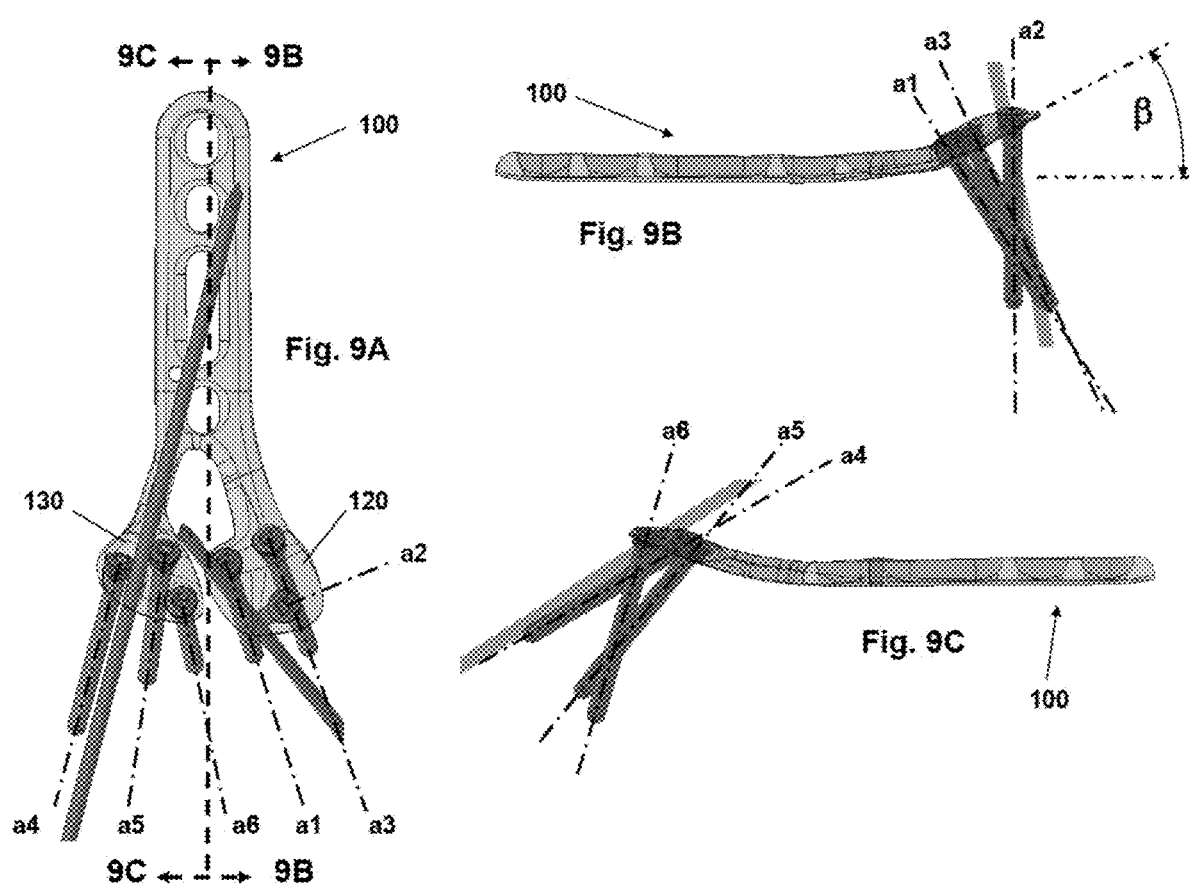

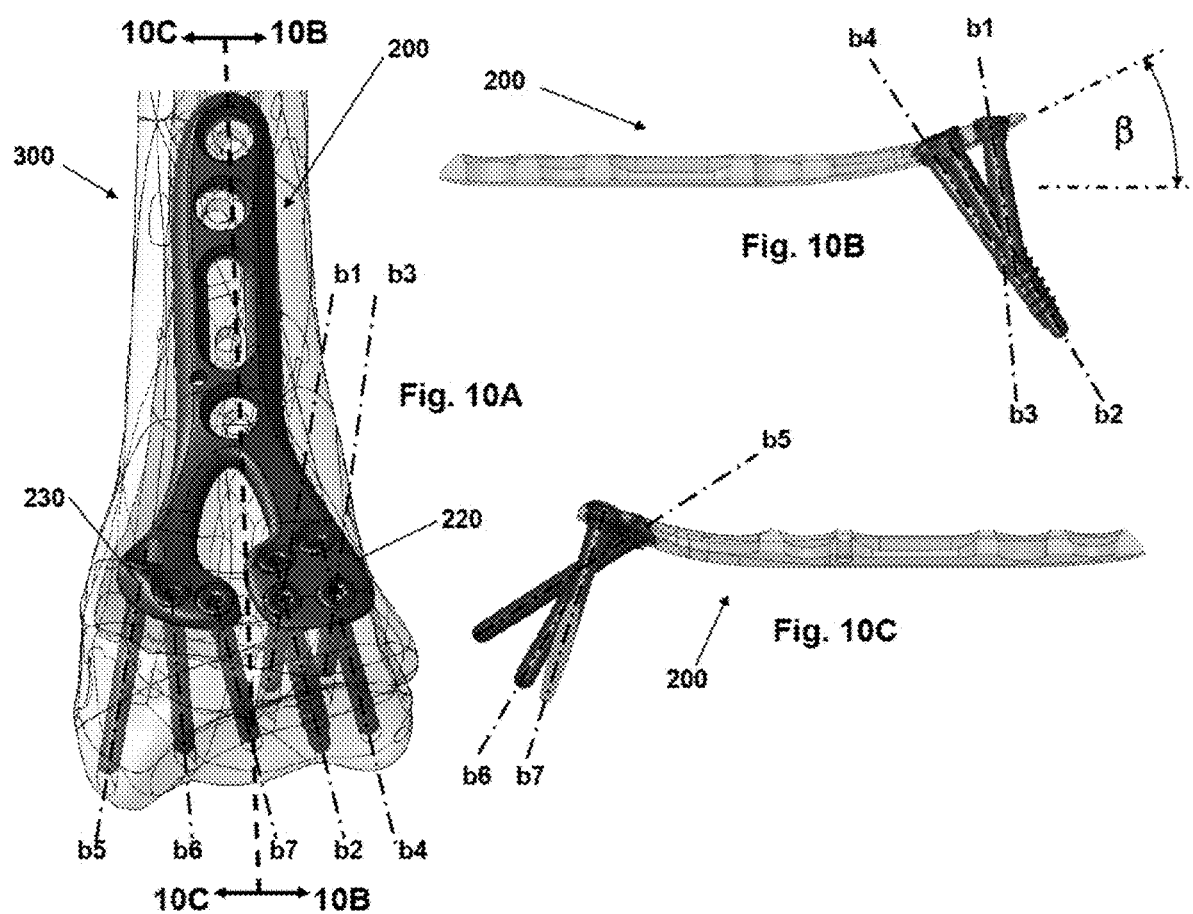

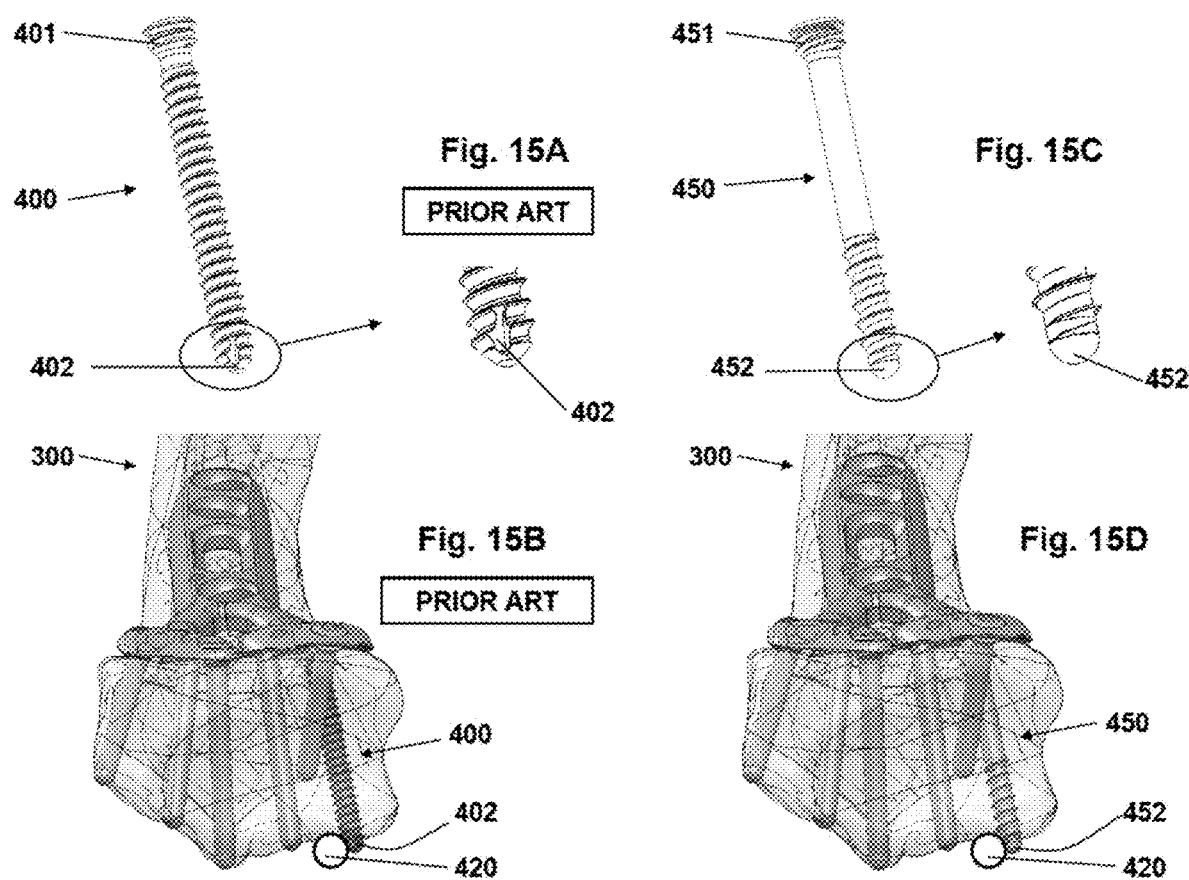

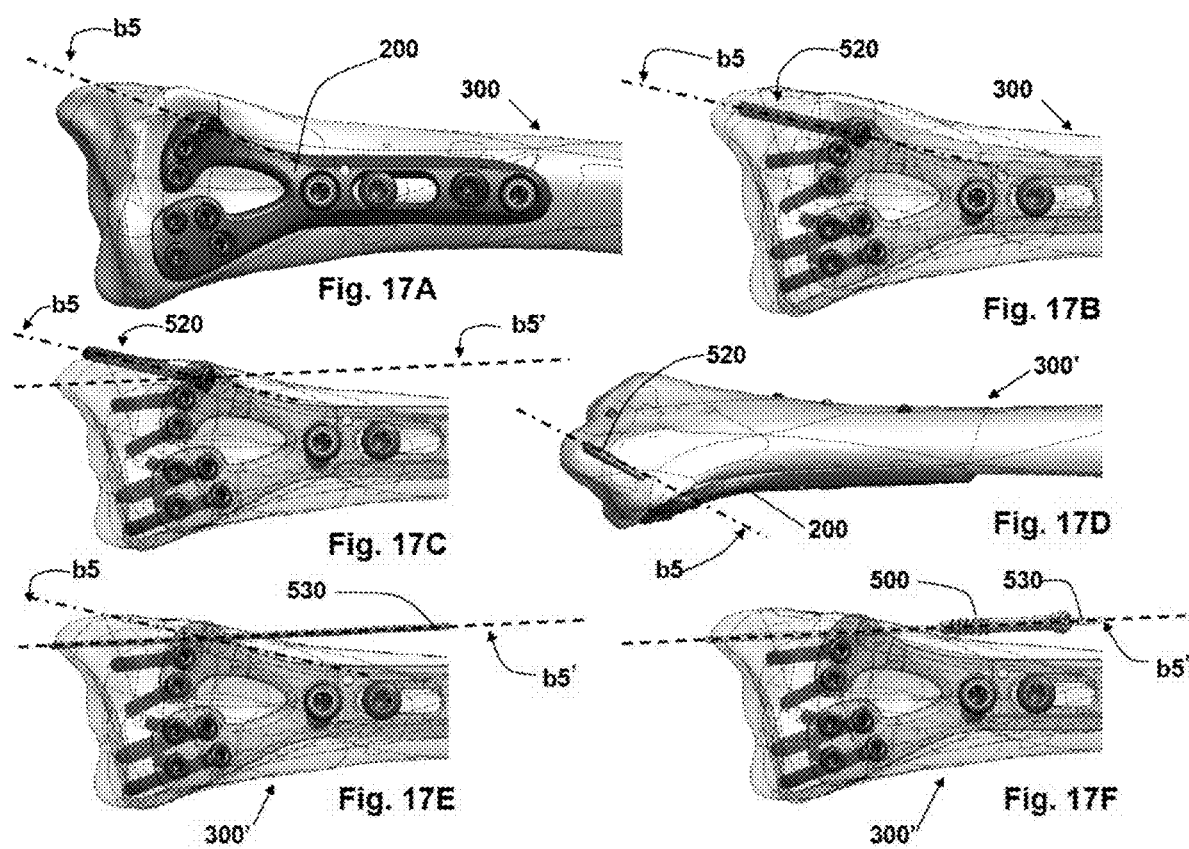

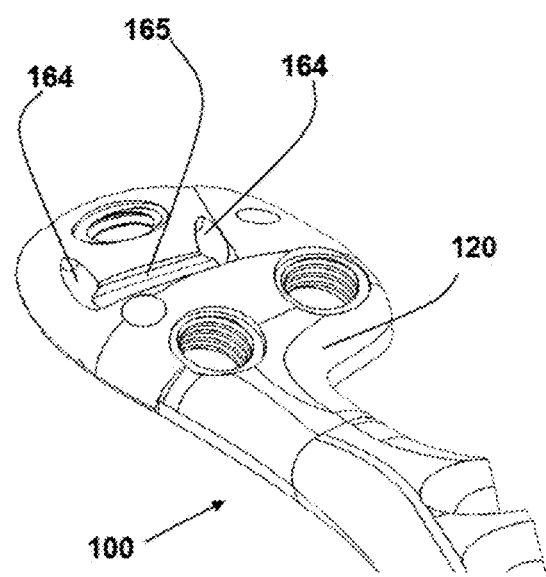 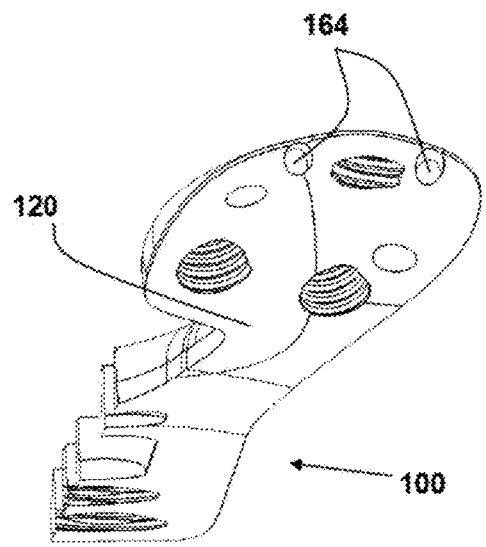
Fig. 18 A  Fig. 18 B

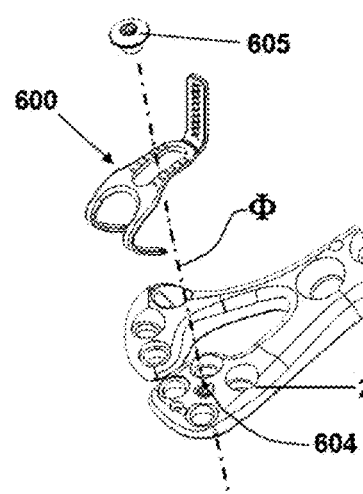
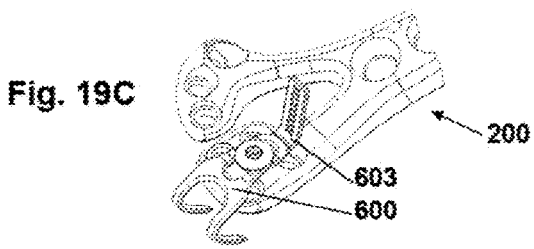
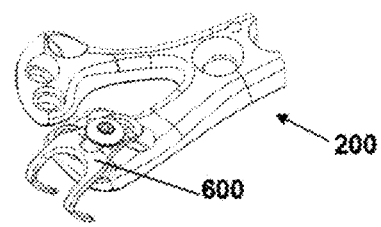
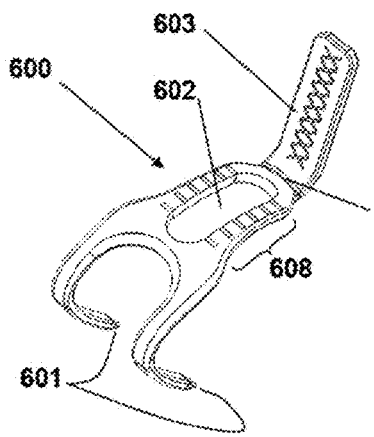
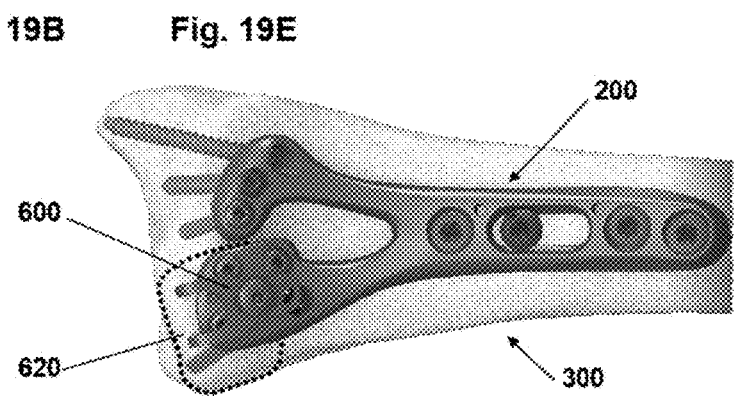

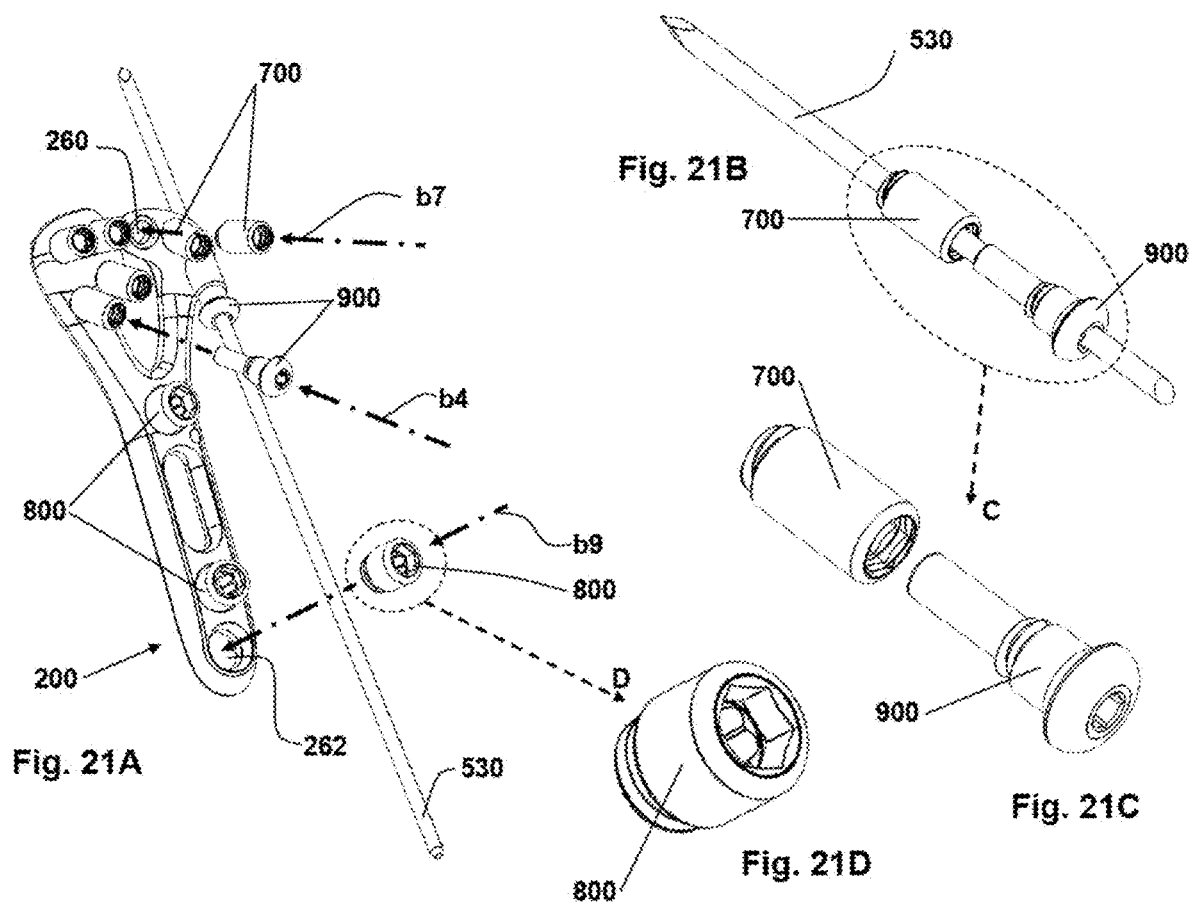

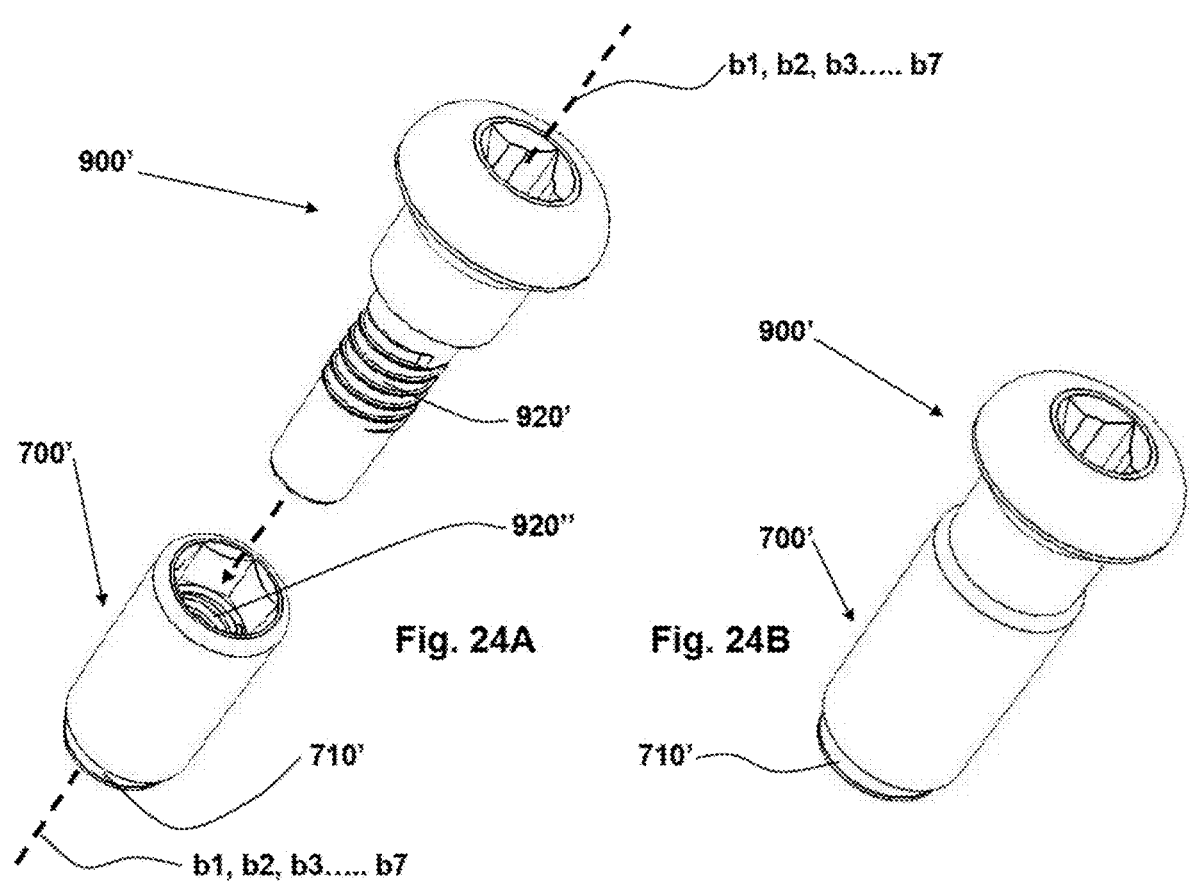

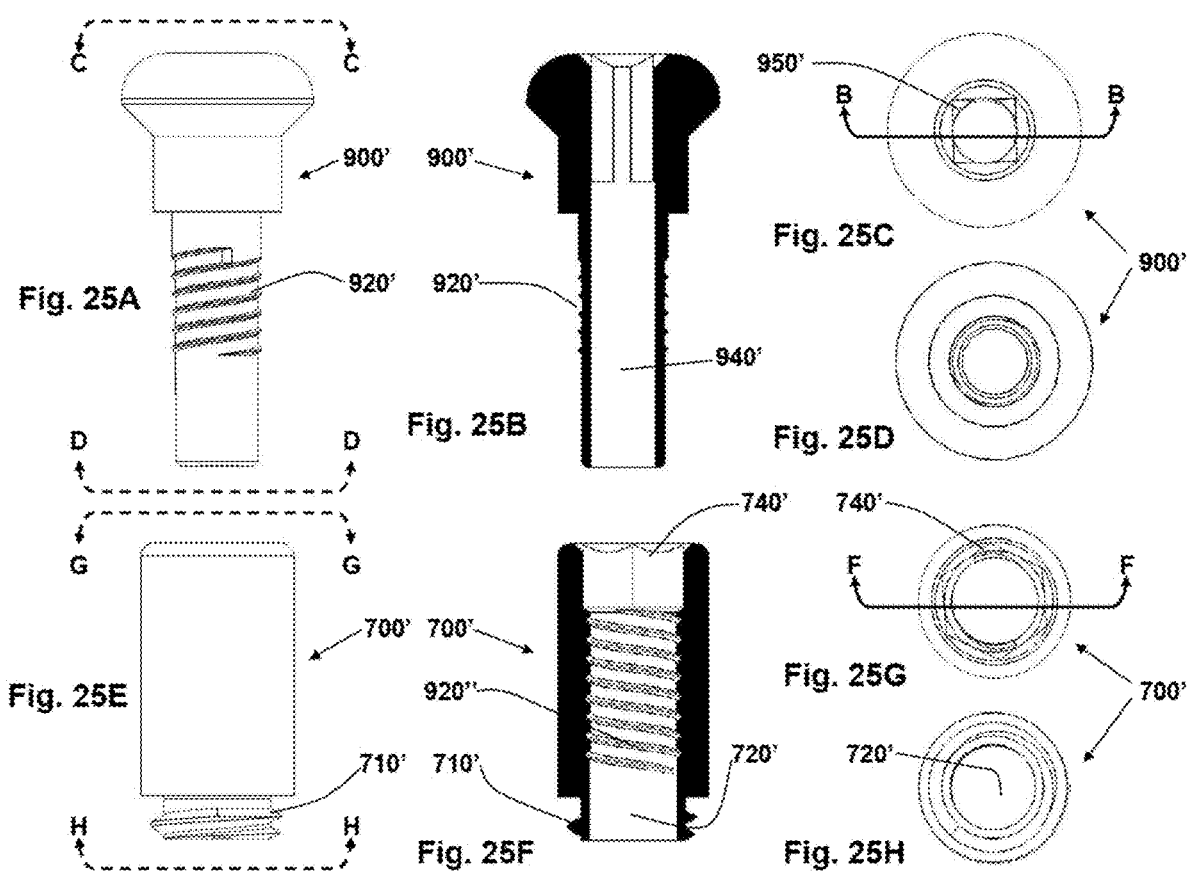

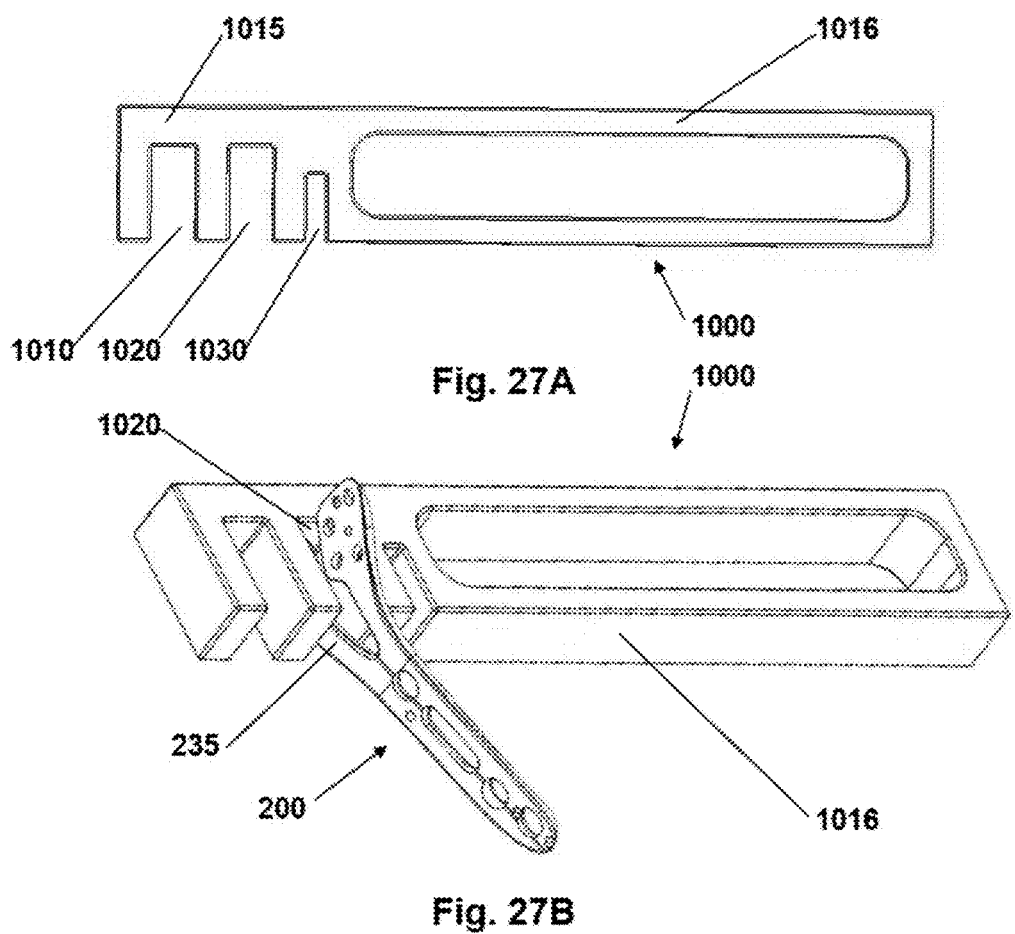

HOOK PLATE AND HOOK PLATE SYSTEM

CLAIM OF PRIORITY

This application is a continuation of U.S. nonprovisional patent application Ser. No. 13/604,931 filed on Sep. 6, 2012, now U.S. Pat. No. 10,603,090 issued on Mar. 31, 2020, which is a continuation-in-part of U.S. nonprovisional patent application Ser. No. 13/366,886 filed on Feb. 6, 2012, now U.S. Pat. No. 8,814,918 issued on Aug. 26, 2014, and claims priority to U.S. provisional patent application Ser. No. 61/531,485 filed on Sep. 6, 2011, Ser. No. 61/536,316 filed on Sep. 19, 2011 and Ser. No. 61/595,986 filed on Feb. 7, 2012. U.S. nonprovisional patent application Ser. No. 13/366,886 filed on Feb. 6, 2012, now U.S. Pat. No. 8,814,918 issued on Aug. 26, 2014, claims priority to U.S. provisional patent application Ser. No. 61/442,595 filed on Feb. 14, 2011, Ser. No. 61/531,485 filed on Sep. 6, 2011 and Ser. No. 61/536,316 filed on Sep. 19, 2011. The contents of all of the above-referenced priority applications are incorporated herein by reference.

FIELD OF INVENTION

The invention relates generally to the fixation of bone fractures and in particular to plates for the volar fixation of fractures of the distal radius.

Background of the Invention

Fracture fixation plates for the distal radius are known in the art. In particular, volar fracture fixation plates for the treatment of the Colles' fracture are frequently used. While many existing volar plates are effective, in many instances they do not provide the means for: a.) good visualization of the fracture; b.) achieving good contact between the plate and the bone; c.) the need to target particular bone fragments; d.) the fixation of small volar marginal fragments and e.) accommodating for conditions such as morbidity of the patient in the form of osteoporotic diaphyseal bone. Furthermore, in a small but significant number of cases, known fracture fixation plates and/or the fasteners attached thereto can impinge upon flexor and/or extensor tendons, resulting in post-operative tendon injury or rupture.

SUMMARY OF THE INVENTION

It is among the objects of this invention to overcome the limitations of the heretofore-known devices by providing inventive features to achieve: a.) superior fixation of the plate to osteoporotic diaphyseal bone; b.) improved visualization of the fracture line; c.) intraoperative adjustability to achieve better contact of the plate and the bone; d.) reduction of the risk of post-surgery flexor and extensor tendon rupture; e.) improved fixation of small volar marginal fragments; f.) improved targeting and fixation of particular fractured bone fragments and g.) reduction of the time required to perform a surgical procedure to install a volar plate.

Although the invention is illustrated and described herein as embodied in a volar fracture fixation plate for the distal radius it is nevertheless not intended to be limited to only the details shown, since various modifications and structural changes may be made therein without departing from the spirit of the invention and within the scope and range of equivalents of the claims.

The construction of the invention, however, together with additional objects and advantages thereof will be best understood from the following description of the specific disclosed embodiments when read in connection with the accompanying drawings.

For purpose of the descriptions of the invention that follow, "bottom" refers to the bone contacting surface of a plate and "top" refers to the opposite surface.

BRIEF DESCRIPTION OF THE DRAWINGS

FIG. 1 is a top view of a fracture fixation plate in accordance with the present invention.

FIG. 2 is a bottom view of a fracture fixation plate in accordance with the present invention.

FIG. 3 is an additional top view of the fracture fixation plate of FIG. 1 showing additional features of the present invention.

FIG. 4 is an additional bottom view of the fracture fixation plate of FIG. 2 showing additional features of the present invention.

FIG. 5 is a top orthogonal view of a fracture fixation plate in accordance with the present invention illustrating the skew axes defined by holes in the ulnar head portion of the fracture fixation plate.

FIG. 6 is top orthogonal view of a fracture fixation plate in accordance with the present invention illustrating the skew axes defined by holes in the radial head portion of the fracture fixation plate.

FIG. 7 is a top orthogonal view of an alternate embodiment of a fracture fixation plate in accordance with the present invention illustrating the skew axes defined by holes in the ulnar head portion of the fracture fixation plate.

FIG. 8 is top orthogonal view of an alternate embodiment of a fracture fixation plate in accordance with the present invention illustrating the skew axes defined by holes in the radial head portion of the fracture fixation plate.

FIG. 9A is a top view (semi-transparent for clarity) of a fracture fixation plate in accordance with the present invention with bone fasteners and K-wires installed therein.

FIG. 9B is a longitudinal cross section of the fracture fixation plate in FIG. 9A showing the ulnar side of the fracture fixation plate.

FIG. 9C is a longitudinal cross section of the fracture fixation plate in FIG. 9A showing the radial side of the fracture fixation plate.

FIG. 10A is a top view of a fracture fixation plate in accordance with an alternate embodiment of the present invention with bone fasteners installed therein, and superimposed on a human radius bone to illustrate its relative positioning.

FIG. 10B is a longitudinal cross section of the fracture fixation plate in FIG. 10A showing the ulnar side of the fracture fixation plate.

FIG. 10C is a longitudinal cross section of the fracture fixation plate in FIG. 10A showing the radial side of the fracture fixation plate.

FIGS. 15A and 15B show, respectively, prior art threaded fastener and the relative positioning between an extensor tendon and the prior art threaded fastener affixed to a fracture fixation plate installed on the volar aspect of a human radius bone.

FIGS. 15C and 15D show, respectively, a threaded fastener in accordance with the present invention and the relative positioning between an extensor tendon and a threaded fastener in accordance with the present invention affixed to a fracture fixation plate installed on the volar aspect of a human radius bone.

FIGS. 17A-17I illustrate the procedure for installing a variable angle cannulated fastener of FIGS. 16A-16B FIG. 18A is a partial top orthogonal view of an alternate embodiment of a fracture fixation plate in accordance with the present invention illustrating suture holes and a communicating channel therebetween.

FIG. 18B is a bottom orthogonal view of the fracture fixation plate in FIG. 18A.

FIGS. 21A-21D illustrate the assembly of head drill guides, body drill guides, K-wire aiming guides, and K-wires relative to a fracture fixation plate in accordance with the present invention.

FIGS. 24A-24B illustrate the assembly of alternative embodiments of a head drill guide and a K-wire aiming guide in accordance with the present invention.

FIGS. 25A-25D illustrate the alternative embodiment of a K-wire aiming guide of FIGS. 24A-24B in accordance with the present invention.

FIGS. 25E-25H illustrate the alternative embodiment of a head drill guide of FIGS. 24A-24B in accordance with the present invention.

FIGS. 27A-27B illustrate a plate bender in accordance with the present invention and the method of engagement of same with a fracture fixation plate in accordance with the present invention.

DETAILED DESCRIPTION OF THE INVENTION

Figure 11:
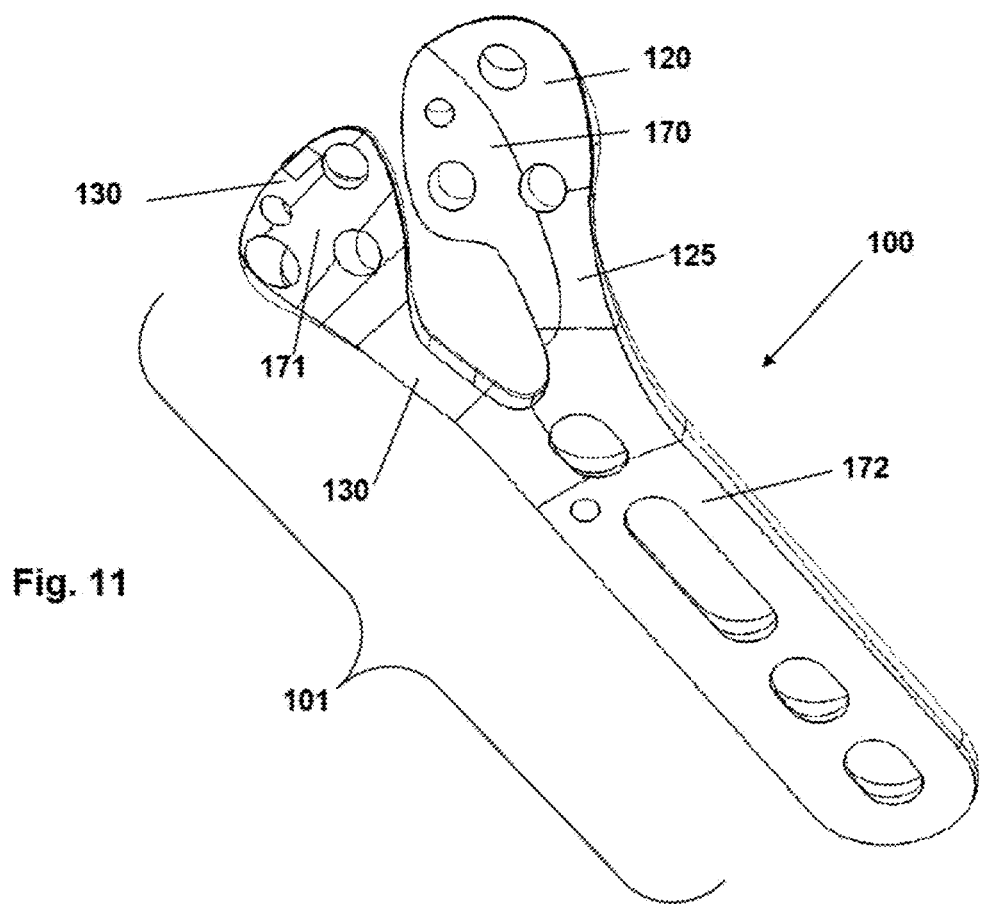
FIG. 11 is a bottom orthogonal view of a fracture fixation plate in accordance with the present invention illustrating various portions of the bone contacting surface of the fracture fixation plate.

Referring to FIGS. 1 and 2, a generally "Y" shaped volar fracture fixation plate 100 is shown having a bone contacting surface 101 and an opposite surface 102, a straight or slightly curving elongated body portion 110 having a proximal end and a distal end and a plurality of independently adjustable head portions 120, 130. The plurality of head portions are angled relative to the body portion 110 about ulnar lateral axis u1 and radial lateral axis r1 that diverge distally at an angle α not less than 20 degrees and not greater than 45 degrees. In one embodiment of the present invention, for use as a volar radius fixation plate, the plurality of head portions are embodied as an ulnar head portion 120 and a radial head portion 130. Head portions 120 and 130 are independently connected to body portion 110, respectively, by ulnar neck portion 125 and radial neck portion 135 which branch out angularly from the distal end of body portion 110 and are independently adjustable. Body portion 110 is intended to be anchored to the diaphysis portion of a bone while ulnar and radial head portions 120 and 130 are adapted to anchor, respectively, the ulnar and radial metaphyseal fragments of a fracture. The gap 140 formed between head portions 120 and 130 as well as between neck portions 125 and 135 allows for good visualization of the fracture line and to accommodate the passage of flexor tendons without impingement.

The volar fracture fixation plate 100 of FIGS. 1-2 corresponds to a volar plate to be installed on the volar aspect of the right human distal radius. A volar plate for installation on the volar aspect of the left human distal radius (not shown) is a mirror image of volar plate 100, identical in all other respects and a further embodiment of the instant invention. It should also be understood that all volar plates of the instant invention referred to herein can be made for the right or the left distal radius and in different sizes to accommodate varying anatomies.

Referring now to FIGS. 1-4 radial head portion 130 of fracture fixation plate 100 includes a plurality of threaded holes 160. In this particular embodiment, the radial head portion 130 includes three threaded holes 160. The threaded holes 160 are arranged non-linearly, e.g.: as vertices of a triangle if three holes 160 are present. In alternate embodiments, if more than three threaded holes 160 are present, the holes are arranged as vertices of a polygon. Holes 160 are intended to receive bone fasteners (i.e.: screws or pegs, solid or cannulated) having threaded heads that are adapted to engage the threads of holes 160 in either: a.) a fixed angle relationship (i.e.: along the axis of a hole 160) or b.) a variable angle relationship (i.e.: along an axis selected intraoperatively by the surgeon, non-collinear with the axis of a hole 160). Likewise, ulnar head portion 120 includes a plurality of holes of type 160, similarly arranged and having similar functionality to those in radial head portion 130.

Referring again to FIGS. 1-4, radial head portion 130 of fracture fixation plate 100 optionally includes at least one non-threaded hole 161. Holes 161 are intended to receive complimentarily sized Kirschner wires (hereinafter "K-wires") therethrough in a pre-defined angular relationship to the bone contacting surface 101 of head portion 130. The K-wires (shown in FIGS. 9A, 9B and 9C) enter the plate through the opposite surface 102 and exit the fracture fixation plate through the bone contacting surface 101. Likewise, ulnar head portion 120 is optionally provided with at least one non-threaded hole 161 having identical functionality to those in radial head portion 130 and may optionally be provided with interconnected holes 164 for receiving sutures as will be explained further below.

As further shown in FIGS. 1-4, in the present embodiment, the body portion 110 includes at least one anchoring hole 162, which is threaded and adapted to receive anchoring fasteners with complementarily threaded heads that engage the threads of anchoring holes 162 at a fixed angle relationship (i.e.: collinear to the axes of anchoring holes 162). The axes of threaded holes 162 may optionally be skew (heretofore defined as non-coplanar) relative to each other. Furthermore, the body portion 110 may optionally include one or more non-threaded anchoring slots 163, for receiving compression screws permitting the temporary repositioning of the plate relative to the underlying bone during surgery. Body portion 110 may optionally include one or more holes 161 intended to receive complimentarily sized K-wires for temporary anchoring of the body portion to the bone.

Referring now to FIGS. 5-6, therein is shown one embodiment of a fracture fixation plate 100 having axes a1 through a9 defined by the plurality of holes 160 and 162. The actual number of axes a1, a2 . . . aN in a particular fracture fixation plate is a function of the number of holes 160 and 162 existing in that particular embodiment of the fracture fixation plate. Axes a1, a2 and a3 in ulnar head portion 120 are skew (non-coplanar, as previously defined) relative to each other but exist in planes that are mutually parallel. Axes a4, a5, and a6 in radial head portion 130 are also skew relative to each other and also exist in planes that are mutually parallel. However, the parallel planes where the first set of axes (a1, a2, a3) exist are not parallel to the parallel planes where the second set of axes (a4, a5, a6) exist but, instead, the first set of parallel planes diverges distally relative to the second set of parallel planes. This arrangement is advantageous because skew lines are inherent to the formation of surfaces that mimic the shape of the articular surface of at least one bone in a joint. Axes a7, a8 and a9 in body portion 110 may optionally be skew relative to each other. This is also advantageous since fasteners anchored along skew axes provide better anchorage of the plate to the diaphysis of osteoporotic bone than equivalent fasteners with parallel axes.

Referring now to FIGS. 7-8, therein is shown an alternate embodiment of a fracture fixation plate 200 having axes b1 through b10 defined by the plurality of threaded holes 260 and 262. In this particular embodiment the ulnar head portion 220 defines four threaded holes 260 arranged as vertices of a four-sided polygon. Axes b1, b2, b3 and b4 of the threaded holes 260 in ulnar head portion 220 are skew relative to each other but exist in planes that are parallel. Axes b5, b6 and b7 of the threaded holes 260 in radial head portion 230 are also skew relative to each other and also exist in planes that are parallel. As in the case of fracture fixation plate 100, the parallel planes where the first set of axes (b1, b2, b3 and b4) exist are not parallel to the parallel planes where the second set of axes (b5, b6 and b7) exist but, instead, the first set of parallel planes diverges distally relative to the second set. As previously described in reference to body portion 110, Axes b8, b9 and b10 of threaded holes 262 in body portion 210 are optionally skew relative to each other.

Referring now to FIG. 9A, therein is shown a plan view of fracture fixation plate 100 (transparent, for clarity) indicating the alignment of axes a1, a2, a3 of ulnar head portion 120 and a4, a5 and a6 of radial head portion 130 in an example of one embodiment of the present invention. FIGS. 9B and 9C, respectively, show longitudinal cross sections of fracture fixation plate 100. FIG. 9B shows the ulnar side cross section view of the alignment of axes a1, a2 and a3 of the ulnar head 120. FIG. 9C shows the radial side cross section view of the alignment of axes a4, a5 and a6 on radial head 130. As indicated in FIG. 9B, ulnar head portion 120 and is inclined upwards at an angle β (i.e.: away from the bone contacting surface) not less than 10 degrees and not greater than 30 degrees relative to a plane defined by the peripheral edges of the bone contacting surface of longitudinal body portion 110. Radial head portion 130 is similarly inclined.

Referring now to FIG. 10A therein is shown a perspective view of the distal volar side of a right radius bone 300, transparent for clarity, with an alternate embodiment 200 of the fracture fixation plate of the instant invention superimposed in the correct position on the bone 300 and indicating the alignment of axes b1, b2, b3 and b4 of the threaded holes and the corresponding fasteners of the ulnar head portion 220 and axes b5, b6 and b7 of the threaded holes and the corresponding fasteners of the radial head portion 230. FIGS. 10B and 10C are, respectively, longitudinal cross sections of fracture fixation plate 200. FIG. 10B shows the alignment of axes b1, b2, b3 and b4 of the threaded holes and the corresponding fasteners of ulnar head portion 220. FIG. 10C shows the alignment of axes b5, b6 and b7 of the threaded holes and the corresponding fasteners of radial head portion 230. The alignment of the axes of threaded holes 260 on each of the head portions and, correspondingly, the axes of the bone fasteners installed thereupon, are skew relative to each other to advantageously provide subchondral support of the articular surface at the lunate fossa and scaphoid fossa. As indicated in FIG. 10B, ulnar head portion 220 and is inclined upwards (i.e.: away from the bone contacting surface) at an angle β not less than 10 degrees and not greater than 30 degrees relative to a plane defined by the peripheral edges of the bone contacting surface of longitudinal body portion 210. Radial head portion 230 is similarly inclined.

Referring now to FIG. 11 therein is shown a perspective view of particular portions of the bone contacting surface 101 of one embodiment 100 of the fracture fixation plate of the instant invention. In the ulnar head portion 120 the bone contacting surface 170 is spherically concave. In the radial head portion 130 the bone contacting surface 171 is substantially flat. In the body portion 110 the bone contacting surface 172 is cylindrically concave in relation to the longitudinal axis of the body portion 110. Alternate fracture fixation plate embodiments optionally may include similar geometrical characteristics of the corresponding surfaces.

Figure 12:
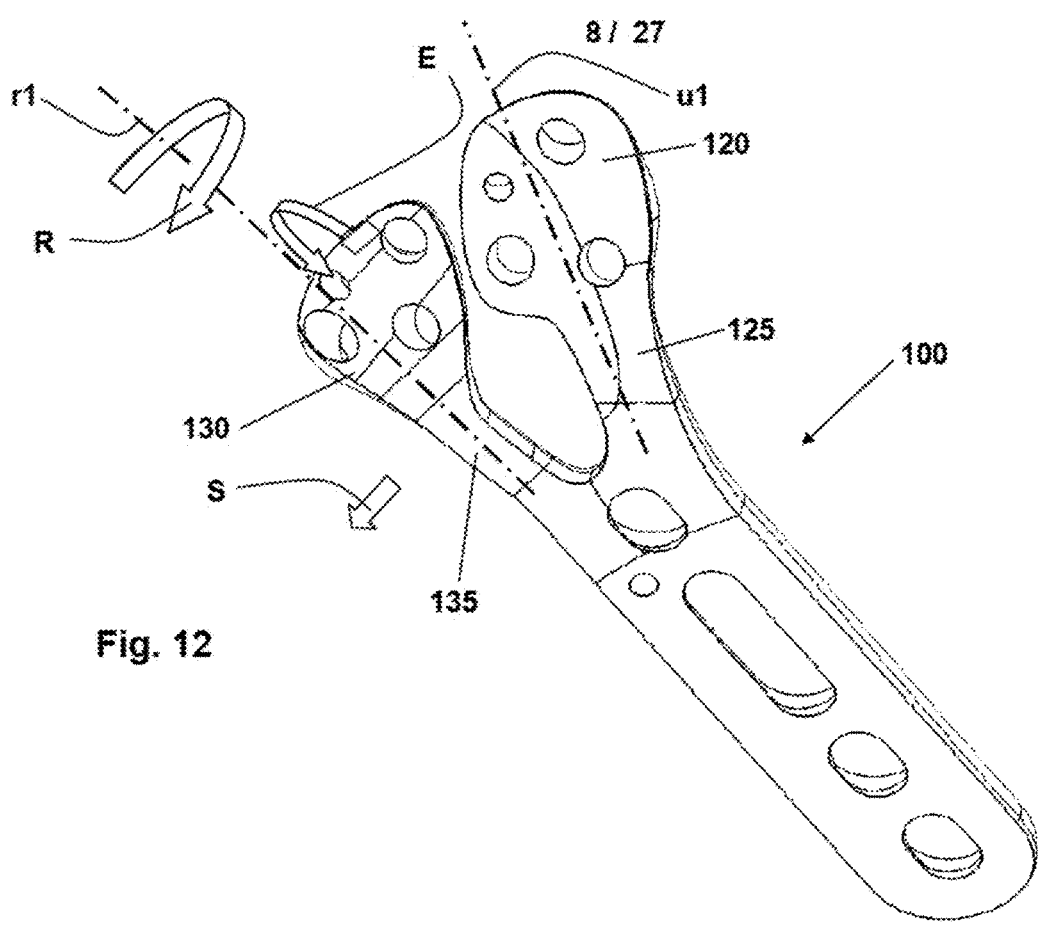
FIG. 12 is a bottom orthogonal view of a fracture fixation plate in accordance with the present invention illustrating the range of adjustability of the position of the radial head portion of the fracture fixation plate.

Referring now to FIG. 12, therein is indicated the range of adjustability of the position of radial head portion 130 of fracture fixation plate 100: 1.) separation S between head portions 130 and 120; 2.) elevation E of the head portion 130 relative to the bone surface and 3.) rotation R of the head portion 130 around the longitudinal axis r1 of radial neck portion 135. The range of adjustability is illustrated by way of example and is not intended to be limiting. The adjustments may be accomplished by the use of plate bending tools, as described further below, to apply appropriate bending and/or torqueing force to radial neck portion 135. The adjustments are advantageous because they facilitate achieving the best contact possible between the bone contacting surfaces of the plate 100 and the underlying bone and bone fragments. Although indicated in FIG. 12 as referring to radial head portion 130, similar positional adjustment can be accomplished on ulnar head portion 120. Alternate embodiments of the fracture fixation plate optionally may include similar positional adjustment features.

Figure 13:
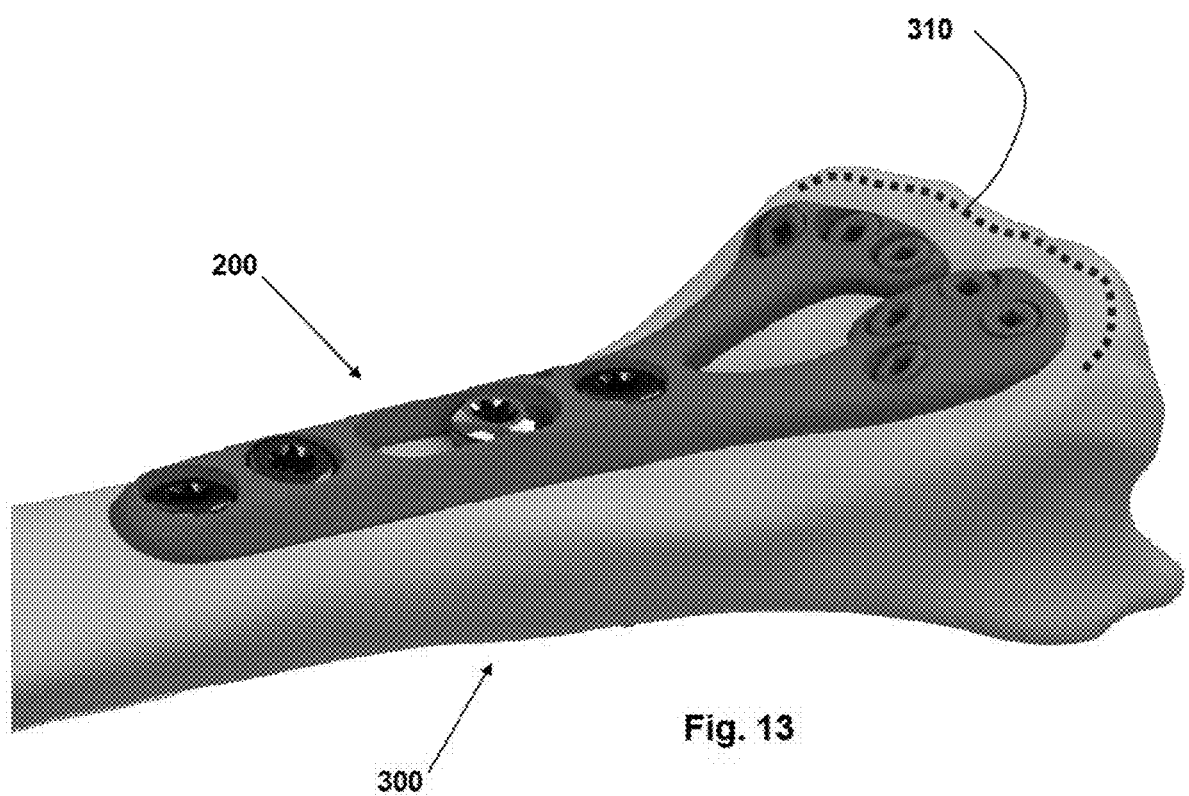
FIG. 13 is a perspective view of an alternate embodiment of a fracture fixation plate in accordance with the present invention installed on the volar aspect of a human radius bone illustrating its position relative to the watershed line.
Figure 14A:
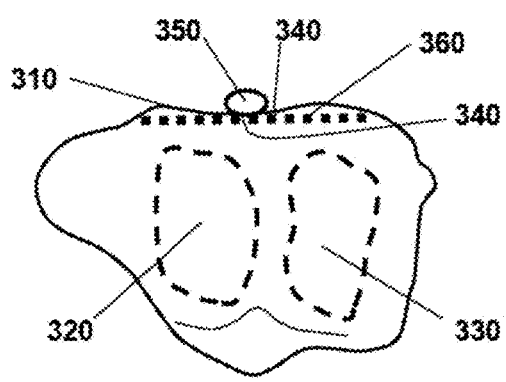
FIGS. 14A and 14B are diagrams illustrating the relative positioning between a flexor tendon in the volar side of the human radius bone and prior art single-headed fracture fixation plates.
Figure 14B:
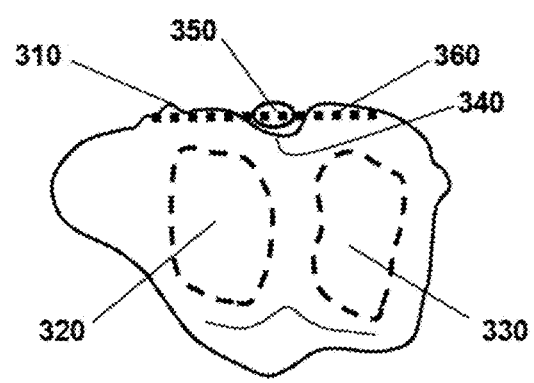
Figure 14C:
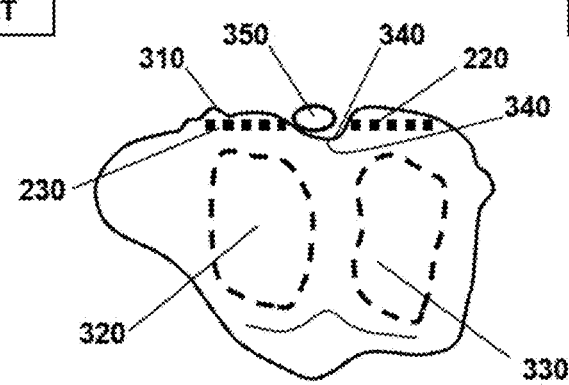
FIG. 14C is a diagram illustrating the relative positioning between a flexor tendon in the volar side of the human radius bone and a fracture fixation plate in accordance with the present invention.

As previously described above, the instant invention provides a fracture fixation plate with a plurality of head portions. This is particularly advantageous for minimizing the risk of post-operative flexor tendon rupture. Referring to FIG. 13 therein is shown a fracture fixation plate 200 correctly installed on the volar side of a distal radius bone 300 just proximal of the watershed line 310, a theoretical line marking the most volar aspect of the volar margin of the distal radius. Referring now to FIG. 14A therein is shown a diagrammatic view of the articular surface of the distal radius, with the volar aspect on the upper side of the diagram, wherein is indicated the scaphoid fossa 320, the lunate fossa 330 and the inter-fossae sulcus 340 and the edge of the watershed line 310. Also shown diagrammatically is a flexor tendon 350 (for example: the Flexor Pollicis Longus). In some patients, the inter-fossae sulcus 340 is relatively shallow at the watershed line 310 and this allows for the correct installation of a prior-art single headed fracture fixation plate 360 (shown dotted) just beyond of the watershed line 310 without post-operative impingement with a flexor tendon 350. However, as shown in FIG. 14B, in other patients, the inter-fossae sulcus 340 is much deeper at the watershed line 310. The installation of a prior-art single headed plate (shown dotted), even if correctly installed proximal of the watershed line 310, can lead to post-operative impingement of said plate and a flexor tendon 350 resulting in tenosynovitis or rupture of the tendon. Referring now to FIG. 14C therein is shown, diagrammatically in dotted line, the installed position of a double headed fracture fixation plate of the instant invention wherein the gap between the radial head portion 230 and the ulnar head portion 220 of the plate allows for the movement of the flexor tendon 350 free of impingement with either of said heads.

In a further advantageous aspect of the instant invention, a threaded fastener is provided for the purpose of minimizing the risk of post-surgical extensor tendon rupture. Referring now to FIGS. 15A-15D and in particular, FIG. 15A therein is shown a prior art threaded fastener 400 having a threaded head 401 for engaging a threaded hole 160 of fracture fixation plate 100 and an opposite bone engaging threaded sharp end 402. If, as can frequently occur and shown in FIG. 15B, the sharp end 402 of the threaded fastener 400 should protrude even minimally through the dorsal aspect of a distal radius bone 300, the sharp end 402 can injure, and even cause rupture, of extensor tendon 420. As shown in FIG. 15C the instant invention provides a threaded fastener 450 having a threaded head 451 for engaging a threaded hole 160 of fracture fixation plate 100 and an opposite, bone engaging, rounded end 452 that is atraumatic. As shown in FIG. 15D, should the threaded fastener 450 protrude as much as 2 mm through the dorsal aspect of the radius, the rounded end 452 of the fastener will not injure or rupture the extensor tendon 420.

As previously discussed, threaded holes 160, 260 of a volar fracture fixation plate 100, 200 are intended to receive fasteners (i.e.: solid pegs or screws) with threaded heads adapted to engage the threads in holes 160, 260. These fasteners can be received at fixed angles, that is, collinearly with the axes of the corresponding hole 160, 260. However, it is one object of the instant invention to provide improved targeting and fixing of particular fractured bone fragments and in many instances this is difficult to accomplish by fixed angle fasteners. Accordingly, to accomplish this purpose, alternative embodiments of the present invention may employ cannulated, variable angle fasteners.

Figure 16A:
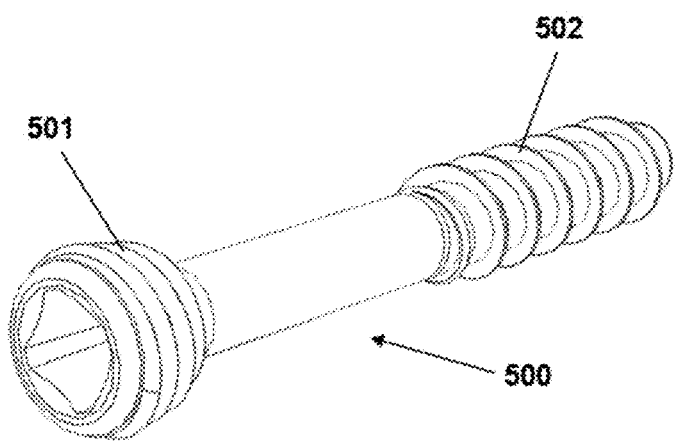
FIG. 16A is a perspective view of a variable angle cannulated fastener in accordance with the present invention.
Figure 16B:
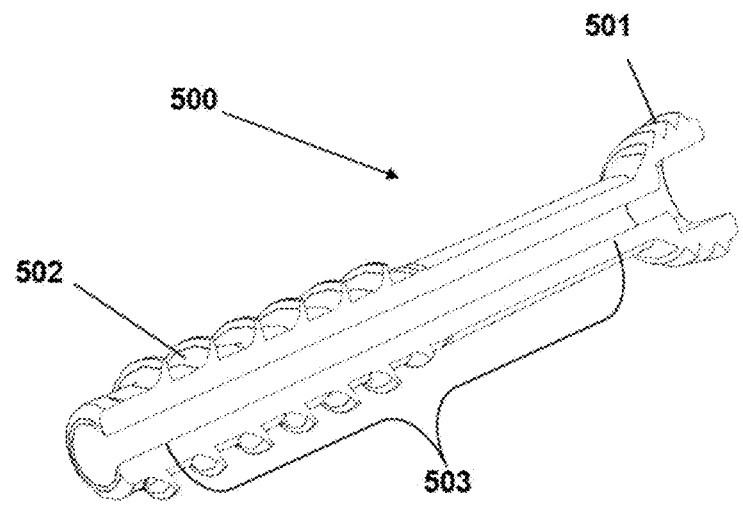
FIG. 16B is a longitudinal, perspective cross-section view of variable angle cannulated fastener in accordance with the present invention.

Referring now to FIGS. 16A-16B therein is shown one embodiment of a cannulated variable angle fastener 500 adaptable for use with the present invention. FIG. 16A shows a perspective view of a variable angle cannulated fastener 500, in this instance a screw, having a tapered threaded head 501 adapted to engage a threaded hole 160, 260 at an angle selected by the surgeon. Variable angle cannulated fastener 500 may optionally have a threaded portion 502 adapted to engaging a bone fragment.

FIG. 16B shows a longitudinal, perspective cross-section view of variable angle fastener 500 with longitudinal cannula 503 extending through the entire length of variable angle fastener 500 and open at both ends. The cannula 503 of variable angle fastener 500 is adapted to be inserted over an appropriately sized K-wire.

Figure 17G:
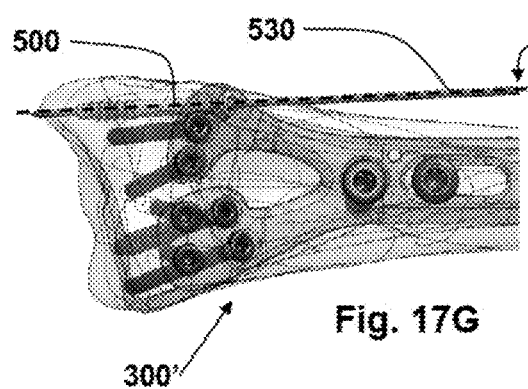

As shown in FIGS. 17A-17I a cannulated variable angle fastener 500 may be used where the fixed angle axis of a threaded hole 160, 260 in a volar plate 100 or 200 would lead to an undesired result. FIG. 17A, 17B show a fracture fixation plate 200 having been correctly installed on the volar side of a distal radius bone 300 with threaded head fastener 520 coaxial with the axis of threaded hole b5. In particular, as shown in FIG. 17B, with the radius bone 300 shown transparent for clarity, axis b5 of the most lateral threaded hole 260 determines that fixed angle fastener 520 inserted therethrough will be anchored into the proper position within the radius bone 300. However, on a smaller radius bone 300' of a different patient, as shown on FIGS. 17C and 17D, a fixed angle fastener 520 inserted following axis b5 would protrude from the bone, possibly causing injury to the surrounding soft tissue. In this situation the surgeon may prefer to select an alternate axis, such as b5' in FIG. 17C, not coaxial with axis b5 of threaded hole 260, through which to insert a fastener.

Figure 17H:
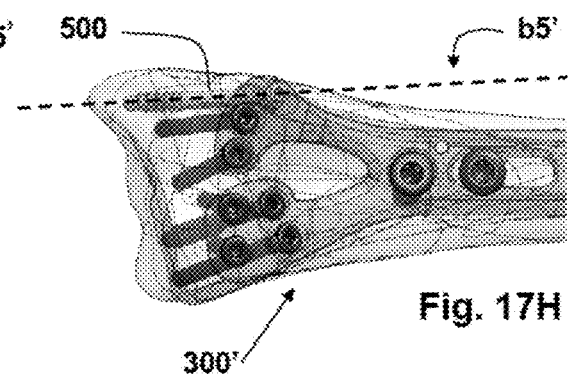
Figure 17I:
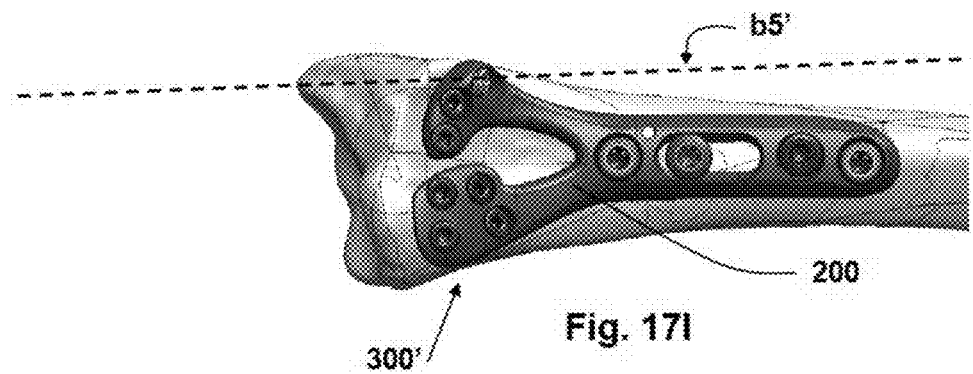

To accomplish this, as shown on FIG. 17E, a K-wire 530 is directed through the threaded hole 260 and drilled into the bone or bone fragment along the surgeon selected axis b5'. Using a cannulated drill, (not shown) the surgeon drills over the K-wire 530 to create a cavity aligned with the desired axis b5'. As further shown in FIGS. 17F-17G, after the cannulated drill is removed, the variable angle cannulated fastener 500 is inserted over the K-wire 530 and torqued with a cannulated driver (not shown) to engage the bone fragment resulting in the correct positioning of the variable angle fastener 500 shown in FIG. 17G. Thereafter, as shown in FIG. 17H, with the radius bone 300' shown transparent for clarity, the K-wire 530 is removed, resulting in the correct installation of variable angle fastener 500 and, consequentially, fracture fixation plate 200 as shown on FIG. 17I.

Since the alternate axis b5' selected by the surgeon is not coaxial with the axis b5 of threaded hole 260 of fracture fixation plate 200, the tapered thread 501 of the head portion of variable angle fastener 500 must be able to fixedly cross-thread into the thread of hole 260. To accomplish this, variable angle fastener 500 can be made of a harder material than plate 200. For example, variable angle fasteners 500 may be made of cobalt chromium while the plate 200 is made of titanium.

As previously indicated above, ulnar head portion 120 of fracture fixation plate 100 may optionally include suture holes 164. Suture holes 164 are non-threaded and mutually communicating and are intended to receive sutures for tension binding small volar marginal fragments of bone. FIGS. 18A and 18B show in greater detail suture holes 164 in ulnar head portion 120 of volar fracture fixation plate 100 and their communicating channel 165 adapted to accommodate the suture knot. If desired suture holes 164 may optionally be provided in radial head portion 130 (not shown). Similar suture holes 164 may optionally be provided in alternate embodiments, for example 200, of the fracture fixation plate of the instant invention.

In addition to, or in substitution of the suture holes 164, the instant invention optionally provides a hook plate for securing and reducing a volar marginal fragment. Referring now to FIGS. 19A-19C therein is shown hook plate 600, intended to be affixed to ulnar head portion 220 of fracture fixation plate 200 to secure a volar marginal fragment. As shown in FIG. 19B, hook plate 600 has a plurality of hook ends 601, a slot 602, a tensioning break-off tab 603 breakable at break-away isthmus 607 and indicia 608 for postoperative detection of hook plate creep. Once a volar marginal fragment is temporarily reduced by the surgeon with a tool (not shown) to the stable portion of the radius bone, the hook plate 600 is superimposed onto the ulnar head portion 220 of a properly installed fracture fixation plate 200 and a retaining screw 605 is inserted through slot 602 and loosely threaded into threaded hole 604 of ulnar head portion 220. The surgeon then engages hook ends 601 into the volar marginal fragment and, applies tension to the hook plate 600 by pulling on tensioning break-off tab 603 until the desired reduction of the volar marginal fragment is achieved. Retaining screw 605 is then tightened into threaded hole 604 and the break-off tab 603 is removed by bending at break-away isthmus 607 and discarded as shown in FIG. 19D. The position of indicia 608 is then recorded for future reference to identify any post-operative creep. FIG. 19E shows the finished construct of hook plate 600 having reduced volar marginal fragment 620 to stable radius bone 300 while securely affixed to the properly installed fracture fixation plate 200.

Figure 19F:
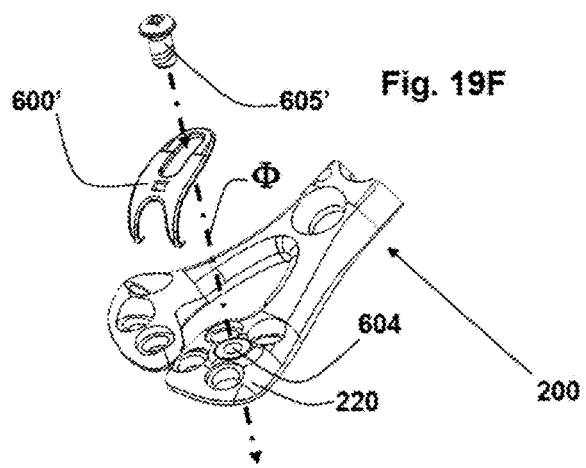
FIGS. 19F-19I illustrate a second embodiment of a hook plate for use in conjunction with a fracture fixation plate in accordance with the present invention to secure a volar marginal fragment.
Figure 19H:
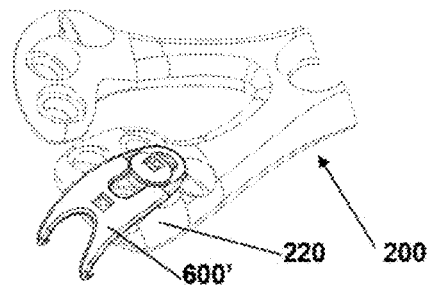
Figure 19G:
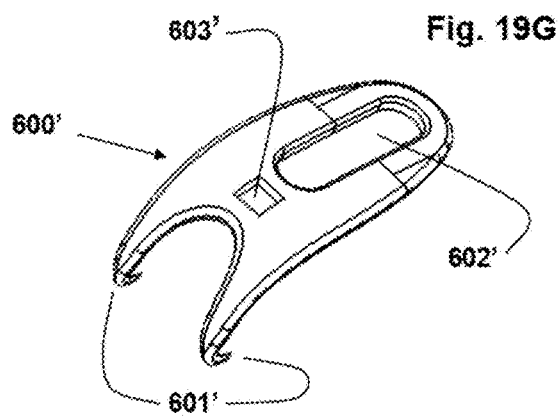
Figure 19:
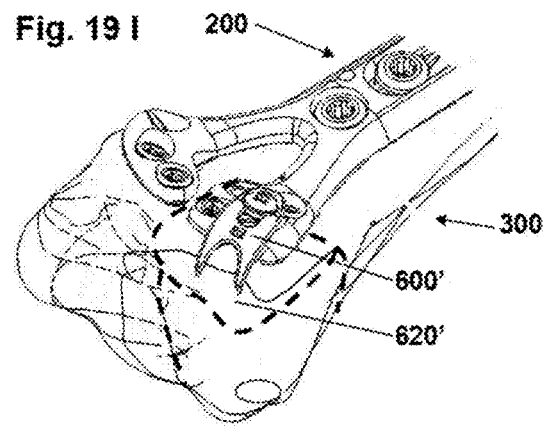
FIGS. 19A-19E illustrate a hook plate for use in conjunction with a fracture fixation plate in accordance with the present invention to secure a volar marginal fragment.
Figure 20A:
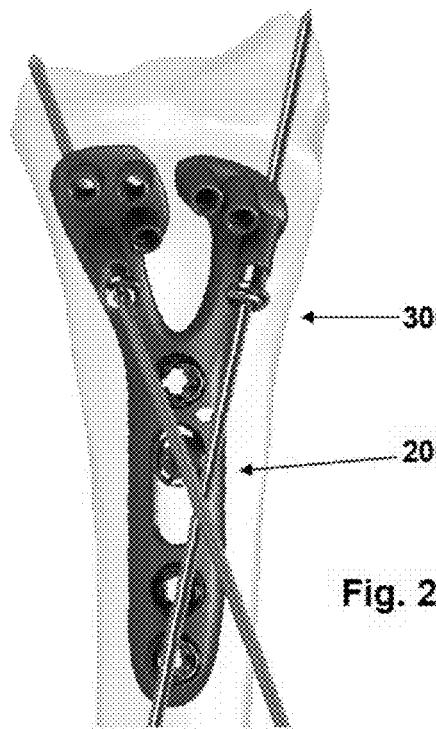
FIGS. 20A-20B illustrate a fracture fixation plate in accordance with the present invention with pre-installed head drill guides, body drill guides, K-wire aiming guides, and K-wires.
Figure 20B:
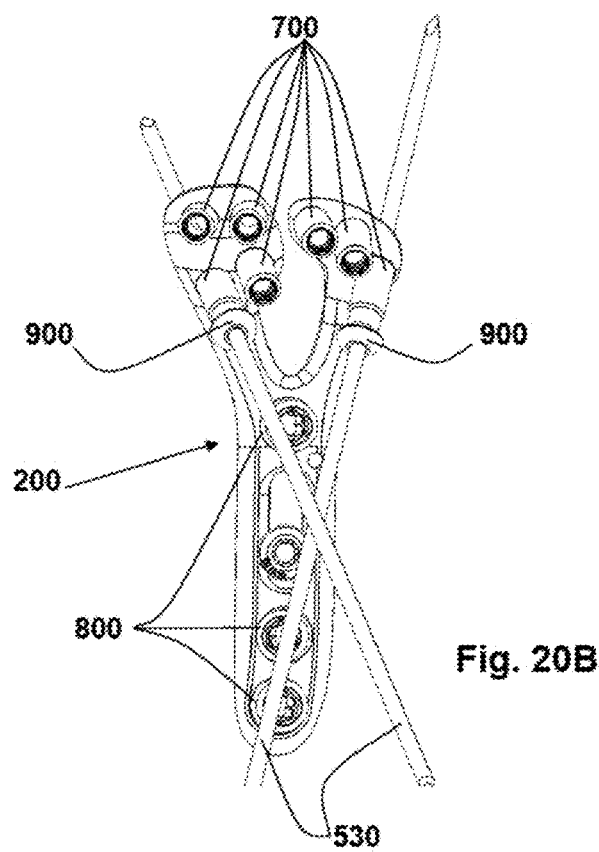

FIGS. 19F-19I show an alternative embodiment of the hook plate 600' wherein the tensioning break-off tab 603 of hook plate 600 is substituted by a tensioning port 603'. After engaging the hook ends 601' into volar marginal fragment 620' the surgeon applies tension by pulling on the tensioning port 603' with a tool (not shown) until the desired reduction is achieved. Retaining screw 605' is then tightened into threaded hole 604 to affix the hook plate 605' to the fracture fixation plate 200 thereby obtaining stable reduction of volar fragment 620' as shown in FIG. 19I.

In addition to being adapted to receive the retaining screw 605, 605', the threaded hole 604 of ulnar head portion 220 can optionally be adapted to receive a K-wire therethrough in a pre-defined orientation for temporary fixation to a portion of the radial bone. As shown in FIGS. 19A and 19F the pre-defined orientation of the axis Q) of threaded hole 604 can be, for example, the orientation that will result in the received K-wire being substantially parallel to a chord drawn, volar to dorsal, between the edges of the anatomical articular surface of the distal radius. Such orientation is at an angle of 98 to 104 degrees distally in reference to a plane defined by the bone contacting surface of the body portion of fracture fixation plate 200.

Although described in reference to fracture fixation plate 200 the hook plates 600, 600', retaining screws 605, 605' and threaded hole 604 can optionally be provided in fracture fixation plate 100 and any other embodiment of the instant invention.

The fracture fixation plates, system and methods of the instant invention include, in their alternative embodiments, accessories that can be useful to reduce the time needed by the surgeon to complete a surgical procedure. Specifically, disclosed herein are drill guides and K-wire aiming guides that can optionally be provided pre-installed on the respective plates 100, 200, thereby obviating the necessity of performing a time consuming installation thereof during surgery. The disclosure of said accessories of the instant invention are shown in FIGS. 20A-26E.

Referring now to FIG. 20A-21D therein are shown a fracture fixation plate 200 with a plurality of pre-installed head drill guides 700, body drill guides 800 and K-wire aiming guides 900. Although described in reference to fracture fixation plate 200 the head drill guides 700, body drill guides 800 and K-wire aiming guides 900 can also be provided or pre-installed in fracture fixation plate 100 and any other embodiment of the fracture fixation plate of the instant invention.

Figure 22A:
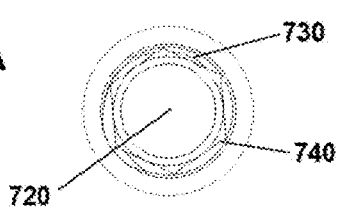
FIGS. 22A-22E illustrate a head drill guide in accordance with the present invention.
Figure 22B:
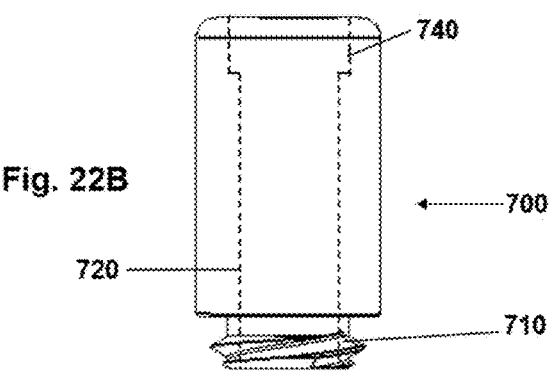
Figure 22C:
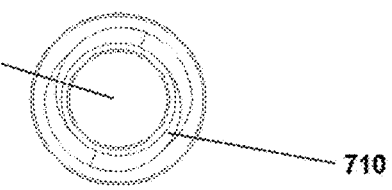
Figure 22D:
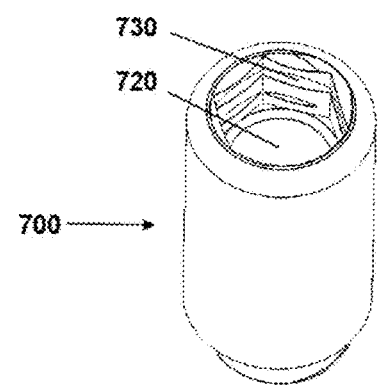
Figure 22E:
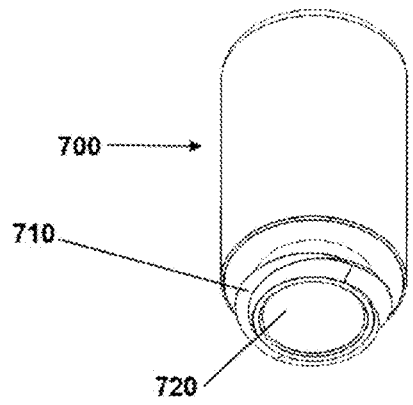

Referring now to FIGS. 22A-22E therein are shown a head drill guide 700 having a proximal end [FIGS. 22A,D], a cylindrical body portion [FIG. 22B] and a distal end [FIGS. 22C,E]. The distal end of head drill guide 700 is provided with an external thread 710 adapted to engage into any threaded hole 260 in any of the head portions of a fracture fixation plate 200 along the axis determined by the thread of said hole 260. The body portion of head drill guide 700 is internally bored, said bore 720 adapted to closely receive and stabilize a drill bit (not shown) inserted therethrough. The proximal end of a head drill guide 700 is provided with an internal thread 730 adapted to engage the threaded central portion of a K-wire aiming guide 900 as further described below and said proximal end is further provided with an internal recess 740 adapted to receive a torque transmitting tool (for example, a hexagonal "Allen" torque transmitting tool—not shown)

Figure 23A:
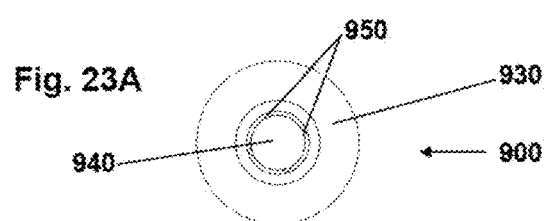
FIGS. 23A-23E illustrate a K-wire aiming guide in accordance with the present invention.
Figure 23D:
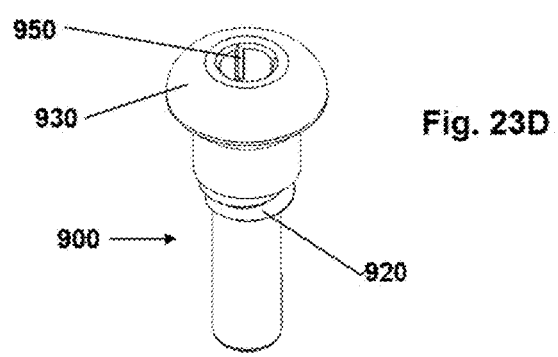
Figure 23B:
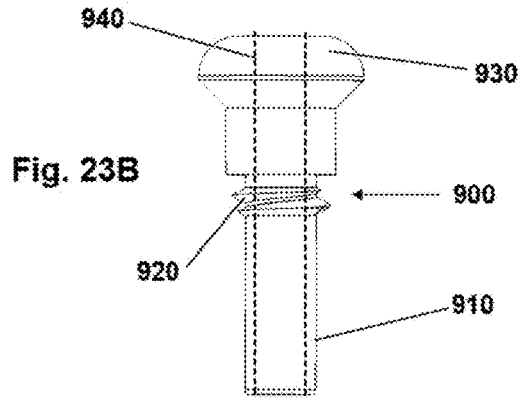
Figure 23E:
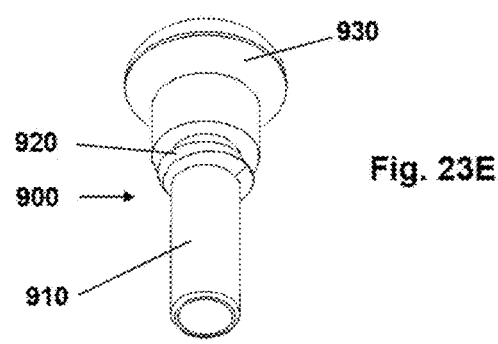
Figure 23C:
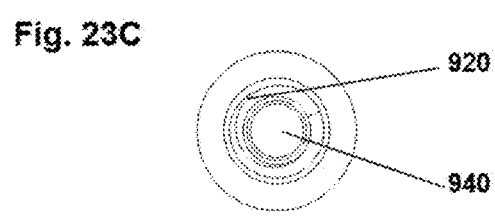
Figure 26A:
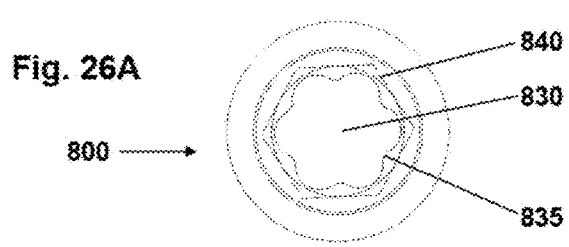
FIGS. 26A-26E illustrate a body drill guide in accordance with the present invention.
Figure 26B:
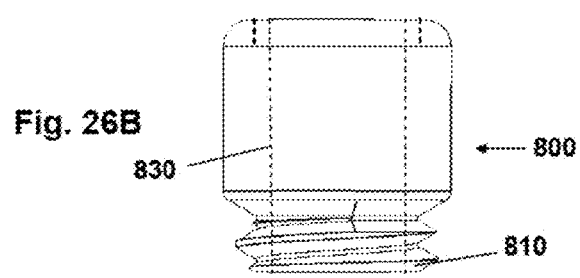
Figure 26C:
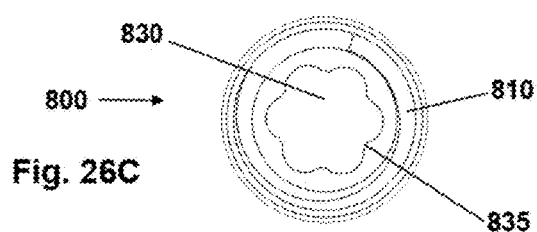
Figure 26D:
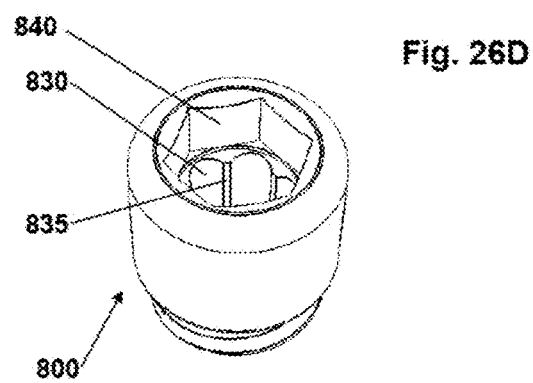
Figure 26E:
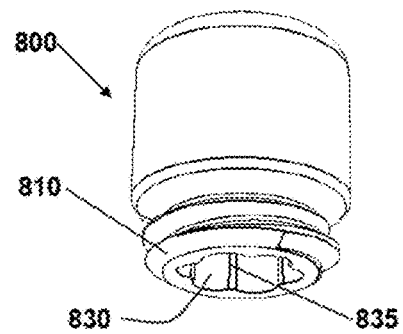

Referring again to FIGS. 21A-21C and in greater detail in FIGS. 23A-23E therein are shown K-wire aiming guides FIGS. 900. Referring now to FIG. 23B K-wire aiming guides 900 are provided with a distal elongated body portion 910, a threaded central portion 920 and a proximal head portion 930. The distal elongated body portion 910 of K-wire aiming guide 900 is adapted to be received inside the bore portion 720 of a head drill guide 700. The externally threaded central portion 920 of K-wire aiming guide 900 is adapted to engage the internal thread 730 of the proximal end of a head drill guide 700. K-wire aiming guide 900 is bored throughout the distal elongated body portion 910, the threaded central portion 920 and the proximal head portion 930, said bore 940 adapted to closely receive and stabilize a K-wire inserted therethrough. As shown in FIGS. 23A and 23D, proximal head portion 930 is provided with an internal recess 950 adapted to receive torque from a torque transmitting tool (for example, a square driver—not shown).

Referring now to FIGS. 24A-25H therein is shown an alternative embodiment of head drill guide 700' and aiming guide 900' wherein are shown external thread 920' and corresponding internal thread 920" for positively engaging aiming guide 900' in head drill guide 700' and thread 710' for coupling head drill guide 700' to a plate 100 or 200 (not shown). During surgery, the aiming guides 900' are removed from the head drill guides 700' after the K-wires they are adapted to guide through bore 940' have been drilled, leaving in place the head drill guide 700' for the further receiving a drill bit (not shown) through bore 720' for drilling pilot holes for the fasteners. In order to assure that, upon removal of the aiming guides 900', the head drill guides 700' remain in place, it is advantageous to provide aiming guide 900' with an external thread 920' that requires less resistance to torque to obtain release than the external threads 710' that couple head drill guides 700' to plates 100, 200. In one particular embodiment of the instant invention this is accomplished by providing a threads 920', 920" with a higher thread angle than external thread 710'. Given the same torque applied to recess 950' of the assembled aiming guides 900' and head drill guide 700', the thread with the higher thread angle will release first. Exemplarily, and not intending to be limiting, threads 920', 920" can be implemented as double lead 2-56 threads while threads 710' can be implemented as 5-44 single lead threads.

Referring again to FIGS. 21A and 21D and in greater detail in FIGS. 26A-26E therein are shown body drill guides 800. Body drill guides 800 have a proximal end [FIGS. 26A and 26D], an externally cylindrical body portion [FIG. 26B] and a distal end [FIGS. 26C and 26E]. The distal end of a body drill guide 800 is provided with an external thread 810 adapted to engage any threaded hole 262 in the body portion 210 of fracture fixation plate 200 along the axis determined by the thread of said hole 262. The body portion of body drill guide 800 is bored throughout, said bore 830 having a non-circular (for example but without limitation, hexalobular) cross section perpendicular to the axis of the bore with at least three flat portions 835, said flat portions adapted to closely receive and stabilize a drill bit inserted therethrough and said non-circular cross-section further capable of accepting torque from a torque transmitting tool (not shown). The proximal end of a body drill guide 800 is additionally provided with an internal recess 840 adapted to receive torque from a different torque transmitting tool (for example, a hexagonal Allen driver—not shown) to permit removal of a body drill guide 800 when its drill guiding purpose has been accomplished.

As referred to above, head drill guides 700, 700' K-wire aiming guides 900, 900' and body drill guides 800 are optionally pre-installed on the fracture fixation plate 100, 200 prior to surgery being performed. Since the installation of K-wires for temporary fixation and the drilling of pilot holes for the installation of bone fasteners require, in many prior-art plates, that the surgeon be provided with and install the appropriate guides during surgery, providing pre-installed guides advantageously leads to a reduction of the time required for completing the surgery.

As previously described above in reference to FIG. 12, plate bending tools may be provided to apply appropriate force to radial neck portion 135, 235 and/or ulnar neck portion 125, 225 of fracture fixation plate 100, 200 to adjust the position of radial head portion 130, 230 and/or ulnar head portion 120, 220 to obtain the best contact possible between the bone contacting surfaces of the plate 100, 200 and the underlying bone and/or bone fragments. Referring now to FIG. 27A therein is shown a plate bender 1000 provided with a plurality of notches 1010, 1020 adapted to engage the radial or ulnar head portions of a fracture fixation plate 100, 200 over the head drill guides 700, 700' and a narrower notch 1030 adapted to engage the radial or ulnar head portions when the head drill guides 700, 700' are not present or have been removed. FIG. 27B shows a plate bender 1000 wherein notch 1020 engages the radial head portion 230 of a fracture fixation plate 200.

Figure 28:
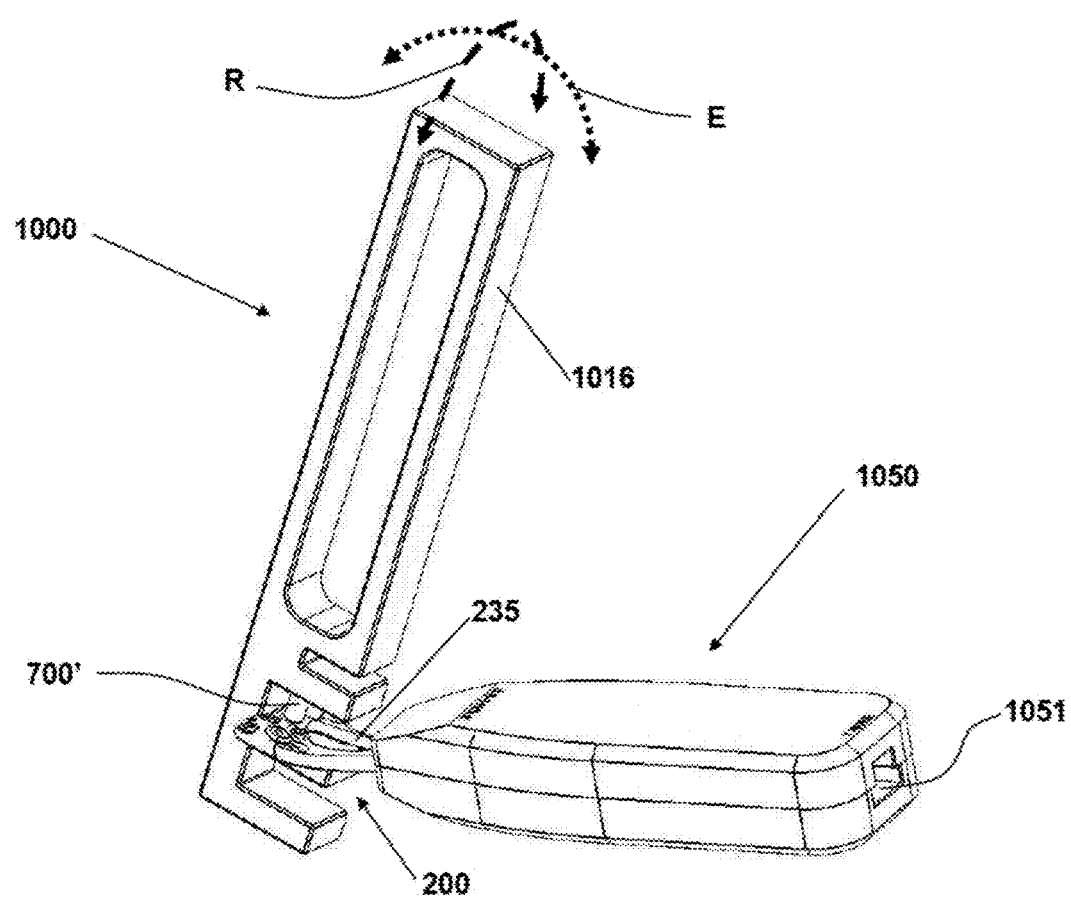
FIG. 28 illustrates the use of a plate bender and a plate holder engaged in bending of a fracture fixation plate in accordance with the present invention.

Referring now to FIG. 28, therein is shown a plate bender 1000 and a complementary plate holder 1050. Plate holder 1050 is provided and adapted to immobilize a fracture fixation plate 100, 200 after said fixation plate has been inserted into retaining notch 1051 on either end of plate holder 1050, while force is applied to plate bender 1000. When said force is applied to plate bender 1000 in a proximal to distal direction, shown as dotted arrow E, the radial neck portion 135, 235 is deformed, resulting in an adjustment of the elevation of radial head portion 130, 230 relative the future underlying bone surface. Conversely, when force is applied to plate bender 1000 in a lateral direction, shown as dashed arrow R the radial neck portion 135, 235 is deformed, resulting in an adjustment of the rotation of radial head portion 130, 230 relative to the future underlying bone surface.

Figure 29A:
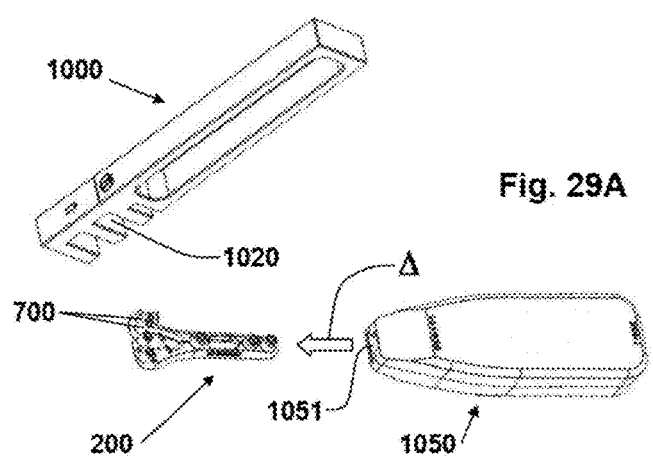
FIGS. 29A-29D illustrate the sequence of steps for assembling a fracture fixation plate with the plate holder and the plate bender in accordance with the present invention for the purpose to applying force to the plate bender to achieve the desired adjustment.
Figure 29B:
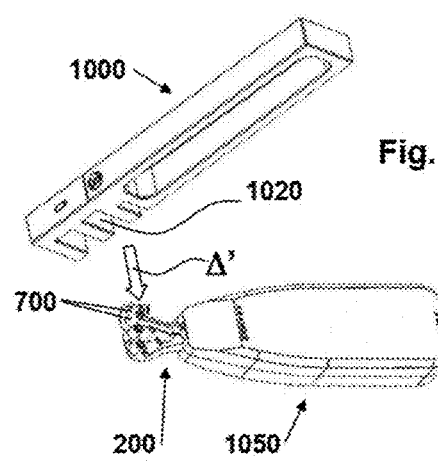
Figure 29C:
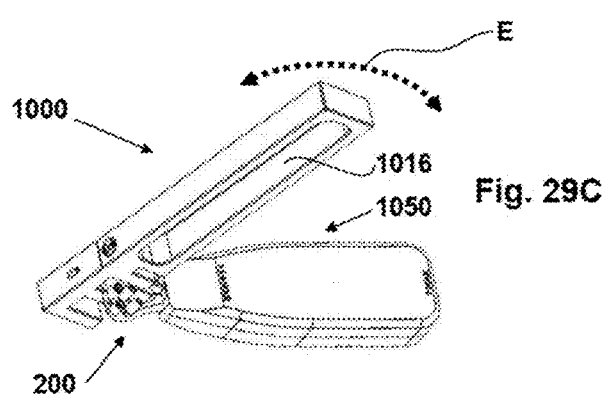
Figure 29D:
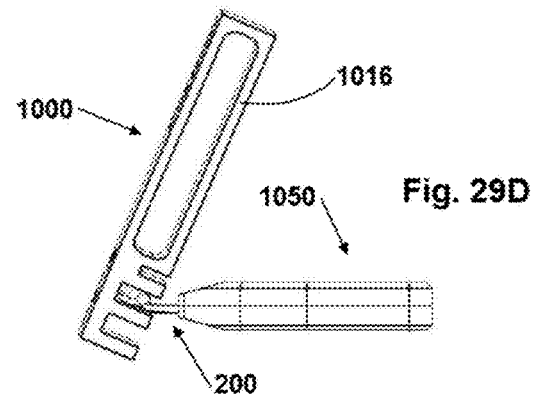

FIGS. 29A-29D illustrate the steps for assembling a fracture fixation plate 100, 200 (200 shown) with the plate holder 1050 and plate bender 1000 for the purpose of applying force to plate bender 1000 to achieve the desired adjustment. Referring now to FIG. 29A, the body portion of plate 100, 200 with body drill guides 800 pre-installed is inserted in the direction of arrow Δ into retaining notch 1051 of plate holder 1050. Once held securely in place by the plate holder 1050 as shown in FIG. 29B the plate bender 1000 is inserted over a head portion of the plate 100, 200 (with head drill guides 700, 700' pre-installed) in the direction of arrow Δ'. Force can then be applied indistinctly in a proximal to distal direction E (shown in FIG. 29C) or a lateral direction to accomplish the desired deformation of the corresponding neck portion 135, 235 of plate 100, 200.

Although described above in connection with a volar fracture fixation plate, accessories, system and method for volar fixation of fractures of the distal radius, these descriptions are not intended to be limiting, as other plates can be made in accordance with the description herein, but of different size or scale, so as to treat other fractures, as needed. As such, although the invention is illustrated and described herein, various modifications and structural changes may be made therein without departing from the spirit of the invention and within the scope and range of equivalents of the claims.

We claim:

1. A hook plate for use in conjunction with a fracture fixation plate, said fracture fixation plate including a bone contacting surface and an opposite surface, said hook plate comprising:
   a substantially rigid plate having a first portion and a second portion;
   the first portion adapted for slidable engagement with, said opposite surface of said fracture fixation plate;
   the second portion configured to wrap around an edge of said fracture fixation plate to engage with a bone fragment and reduce a fracture;
   the first portion being substantially flat and defining a first portion plane;
   the second portion having at least two projections which curve downward to a position below the first portion plane and terminate in hook ends adapted to engage with said bone fragment;
   the first portion including a slot that transects said hook plate from a surface of said hook plate that faces the fracture fixation plate to an opposing surface of said hook plate for engagement with a fastener on said opposite surface of said fracture fixation plate;

said slot being elongated; and the first portion including an elongate member extending distally away from the first portion and upward to a position above the first portion, said elongate member adapted to aid in tensioning of the hook plate prior to tightening of the fastener.

2. The hook plate of claim 1 wherein said elongate member is removable.

3. The hook plate of claim 1 wherein said fastener is a threaded fastener.

4. The hook plate of claim 1 wherein the first portion comprises indicia proximate the slot, said indicia adapted to identify any movement of said hook plate relative to said fracture fixation plate.

5. A fracture fixation apparatus comprising:

a substantially rigid fracture fixation plate including an elongated body portion having proximal and distal ends and defining a longitudinal body axis;

said fracture fixation plate including a head portion adjacent to the distal end of said body portion;

said head portion including a bone contacting surface and an opposite surface;

the bone contacting surface of said head portion being adapted to anchor an ulnar or radial metaphyseal fragment of a fracture;

a substantially rigid hook plate having a first portion and a second portion;

the first portion adapted for slidable engagement with said opposite surface of said head portion;

the second portion configured to wrap around an edge of said head portion to engage a bone fragment and reduce a fracture;

the first portion being substantially flat and defining a first portion plane;

the second portion having at least two projections which curve downward to a position below the first portion plane and terminate in hook ends adapted to engage said bone fragment;

the first portion including a slot that transects said hook plate from a surface of said hook plate that faces the fracture fixation plate to an opposing surface of said hook plate for engagement with a fastener on said opposite surface of said head portion;

said slot being elongated; and the first portion including an elongate member extending distally away from the first portion and upward to a position above the first portion, said elongate member adapted to aid in tensioning of the hook plate prior to tightening of the fastener.

6. The fracture fixation apparatus of claim 5 wherein said elongate member is removable.

7. The fracture fixation apparatus of claim 5 wherein said fastener is a threaded fastener.

8. The fracture fixation apparatus of claim 5 wherein the first portion comprises indicia proximate the slot, said indicia adapted to identify any movement of said hook plate relative to said fracture fixation plate.

* * * * *